US012161606B1

(12) United States Patent
Steyn et al.

(10) Patent No.: US 12,161,606 B1
(45) Date of Patent: Dec. 10, 2024

(54) NETWORK-CONNECTED CONTAINERS HAVING MEDICATION STORED THEREIN

(71) Applicant: Verily Life Sciences LLC, Mountain View, CA (US)

(72) Inventors: Jasper Lodewyk Steyn, San Bruno, CA (US); Jaeden Hutchison, Oakland, CA (US); Madeline Folkerts, San Francisco, CA (US); Jonathan Grossman, San Francisco, CA (US); Charles Hammond, Walnut Creek, CA (US)

(73) Assignee: Verily Life Sciences LLC, Dallas, TX (US)

(*) Notice: Subject to any disclaimer, the term of this patent is extended or adjusted under 35 U.S.C. 154(b) by 0 days.

(21) Appl. No.: 18/346,581

(22) Filed: Jul. 3, 2023

Related U.S. Application Data

(63) Continuation of application No. 17/495,279, filed on Oct. 6, 2021, now Pat. No. 11,737,954.

(60) Provisional application No. 63/088,285, filed on Oct. 6, 2020.

(51) Int. Cl.
| | |
|---|---|
| *G08B 5/00* | (2006.01) |
| *A61J 7/04* | (2006.01) |
| *G08B 5/36* | (2006.01) |
| *G16H 20/13* | (2018.01) |
| *A61J 1/03* | (2023.01) |

(52) U.S. Cl.
CPC ............. *A61J 7/0436* (2015.05); *G08B 5/36* (2013.01); *G16H 20/13* (2018.01); *A61J 1/03* (2013.01); *A61J 2200/30* (2013.01); *A61J 2200/70* (2013.01)

(58) Field of Classification Search
CPC ........ A61J 7/0436; A61J 1/03; A61J 2200/30; A61J 2200/70; G08B 5/36; G16H 20/13
USPC ...................................................... 340/815.4
See application file for complete search history.

(56) References Cited

U.S. PATENT DOCUMENTS

| | | |
|---|---|---|
| 5,370,622 A | 12/1994 | Livingston et al. |
| 6,771,165 B2 | 8/2004 | Burg et al. |
| 6,937,617 B2 | 8/2005 | Rakib et al. |
| 6,983,031 B2 | 1/2006 | Wheatley |
| 7,040,776 B2 | 5/2006 | Harrell et al. |
| 7,336,194 B2 | 2/2008 | Hillman et al. |

(Continued)

FOREIGN PATENT DOCUMENTS

| | | |
|---|---|---|
| CN | 208906860 U | 5/2019 |
| EP | 2155288 A1 | 2/2010 |

(Continued)

*Primary Examiner* — Tai T Nguyen
(74) *Attorney, Agent, or Firm* — Perkins Coie LLP

(57) ABSTRACT

Introduced here are containers designed to promote compliance with regimens for administering the medications stored therein. These containers have various features that allow them to be more easily managed by the individuals to whom the medications were prescribed. Some features improve the ease with which containers communicate with individuals. These features may enable information to be more easily input by individuals and/or output for individuals in a comprehensible manner. Other features improve the mechanical or electrical durability of containers. Such features may enable the containers to be used by individuals over the course of several days, weeks, or months without worrying about structural damage or loss of power.

19 Claims, 15 Drawing Sheets

(56) References Cited

U.S. PATENT DOCUMENTS

| | | | |
|---|---|---|---|
| 7,366,675 B1 | 4/2008 | Walker et al. | |
| 8,754,769 B2 | 6/2014 | Stein et al. | |
| 9,163,826 B1 | 10/2015 | Citrin | |
| 9,395,479 B2 | 7/2016 | Holman et al. | |
| 9,621,974 B2 | 4/2017 | Mohindra et al. | |
| 10,456,326 B2 | 10/2019 | Wiser et al. | |
| 2003/0105430 A1 | 6/2003 | Lavi et al. | |
| 2007/0126851 A1 | 6/2007 | Yamazaki | |
| 2009/0140251 A1 | 6/2009 | Yamazaki | |
| 2009/0294521 A1 | 12/2009 | De | |
| 2012/0056000 A1 | 3/2012 | Shores | |
| 2013/0218588 A1 | 8/2013 | Kehr et al. | |
| 2016/0342748 A1* | 11/2016 | Gulfo | G06Q 30/0639 |
| 2017/0109498 A1* | 4/2017 | Childress | G16H 20/13 |
| 2017/0124284 A1 | 5/2017 | Mccullough et al. | |
| 2018/0204636 A1* | 7/2018 | Edwards | G16H 40/67 |
| 2019/0293856 A1 | 9/2019 | Danziger | |

FOREIGN PATENT DOCUMENTS

| | | | |
|---|---|---|---|
| WO | 9217231 A1 | 10/1992 | |
| WO | 2005020872 A2 | 3/2005 | |

\* cited by examiner

1200

1201

| Identify a primary switch assembly from amongst a plurality of switch assemblies |
|---|

1202

| Identify all switch assemblies other than the primary switch assembly as secondary switch assemblies |
|---|

1203

| Cause an appropriate bias voltage to be suppled to the resistor of each secondary switch assembly via the corresponding input/output (IO) pin |
|---|

1204

| Monitor for signals from the primary switch assembly |
|---|

1205

| Determine whether the cap has experienced a change in state based on the signals generated by the primary switch assembly |
|---|

FIGURE 12

NETWORK-CONNECTED CONTAINERS HAVING MEDICATION STORED THEREIN

CROSS-REFERENCE TO RELATED APPLICATIONS

This application is a continuation of U.S. application Ser. No. 17/495,279, titled "Network-Connected Containers Having Medication Stored Therein" and filed on Oct. 6, 2021, which claims priority to U.S. Provisional Application No. 63/088,285, titled "Network-Connected Containers Having Medication Stored Therein" and filed on Oct. 6, 2020, which is incorporated by reference herein in its entirety.

TECHNICAL FIELD

Various embodiments concern containers designed to promote compliance with regimens for administering the medications stored therein.

BACKGROUND

A pill organizer (also referred to as a "pill container" or "pill box") is a multi-compartment aid designed to promote compliance with a medication regimen (or simply a "regimen") by storing scheduled doses of one or more medications. Many pill organizers have at least one compartment for each day of the week, though other versions have been developed. Some pill organizers have multiple compartments corresponding to different times of the day. For instance, a pill organizer could include a first row of seven compartments in which medications to be administered in the morning are placed and a second row of seven compartments in which medications to be administered in the evening are placed.

Historically, pill organizers have been viewed as a convenient way to reduce the number of errors associated with the administrations of medication(s) required by a regimen. Such errors include administering the wrong dose of a given medication and administering a dose of a given medication at the wrong time. However, evidence of effectiveness of these pill organizers is not strong.

BRIEF DESCRIPTION OF THE DRAWINGS

FIG. 12 includes a flow diagram of a process for controllably activating and then deactivating a plurality of switch assemblies configured to generate signals from which events involving the cap of a container can be inferred.

Figure 1A:
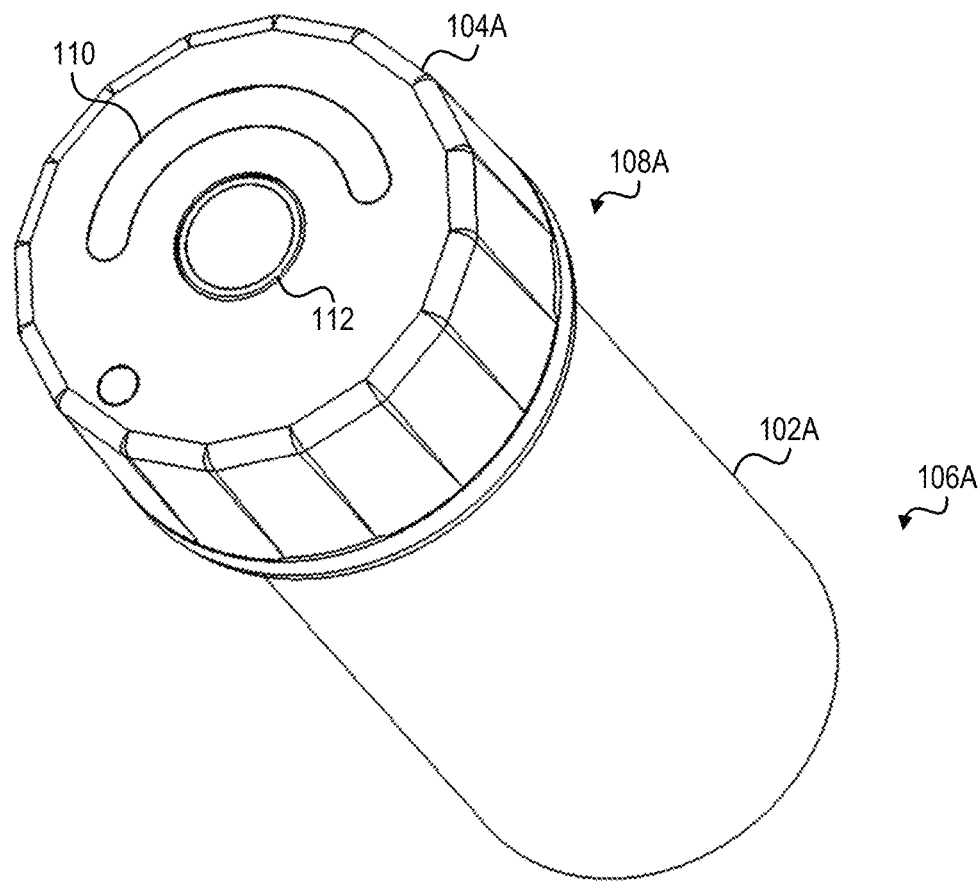
FIGS. 1A-B are perspective views of containers that are able to notify an individual when the medications stored therein are due to be administered or when the containers were last opened.

Various features of the technologies described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the principles of the technology. Accordingly, while specific embodiments are shown in the drawings, the technology is amenable to various modifications.

DETAILED DESCRIPTION

To address the drawbacks of conventional pill organizers, entities have begun developing electronic pill bottles that are designed to alert individuals (also referred to as "patients" or "subjects") when a medication should be administered. Rather than include separate compartments for the doses to be administered over a given interval of time (e.g., a week), an electronic pill bottle will generally include a single cavity in which a bulk supply of medication is stored. Generally, electronic pill bottles are able to communicate with other electronic devices via a network. Accordingly, electronic pill bottles may be referred to as "network-connected bottles" or "smart bottles."

An electronic pill bottle may be designed to communicate, either continually or periodically, with a computer program executing on an electronic device. For instance, an electronic pill bottle may be configured to transmit data regarding administrations of medication to a mobile application executing on a mobile phone associated with the individual responsible for administering the medication stored therein. The computer program may promote compliance with a regimen by generating notifications that alert the individual when doses of medication are due to be administered.

Historically, electronic pill bottles have been designed with several goals in mind. First, an electronic pill bottle should be able to address forgetfulness through on-device notifications (also referred to as "reminders") that can be readily understood. Generally, the term "on-device" refers to reminders that are presented by the electronic pill bottle itself, though the term could also be used to refer to reminders that are presented by an electronic device (e.g., a mobile phone) that is communicatively connected to the electronic pill bottle. Second, an electronic pill bottle should be able to record data related to administrations of medication so that adherence to a regimen can be tracked. Third, an electronic pill bottle should be able to withstand the damage that will inevitably occur as a result of consistent use over an extended period of time. And fourth, an electronic pill bottle should be able to manage its power so that it survives until the bulk supply of medication therein has been depleted. However, electronic pill bottles have failed to accomplish these goals in a consistent, predictable, and cost-efficient manner.

Introduced here, therefore, are containers designed to promote compliance with regimens for administering the medications stored therein. These containers have various features that allow them to be more easily managed by the individuals to whom the medications were prescribed.

Some features improve the ease with which containers communicate with individuals. These features may enable information to be more easily input by individuals and/or output for individuals in a comprehensible manner. For example, a container may be able to communicate the time elapsed since the container was last opened to help a user in the instance where they have forgotten whether they have taken the medication or not. Alternatively, a container may be able to communicate when a dose of medication is due to be administered through the use of a non-written medium that is readily understandable without requiring that the instructions accompanying the prescription be read. As another example, a container may include a limited number of interfaces (e.g., tactile elements such as buttons, keys, and the like) through which input can be provided in order to lessen the likelihood of confusion.

Other features improve the mechanical or electrical durability of containers. Such features may enable the containers to be used by individuals over the course of several days, weeks, or months without worrying about structural damage, loss of power, etc. For example, a container may include one or more shock-absorbing elements that serve to absorb impact energy and inhibit destructive movement of internal components when the container is shaken, dropped, etc. As another example, a container may include a plurality of switch assemblies configured to generate signals from which changes in state (e.g., whether the container has been opened or closed) can be inferred; however, the container may only permit a subset of those switch assemblies to be active at most points in time to lessen power consumption. The plurality of switch assemblies may also contribute to redundancy and reliability of detecting switching events.

Embodiments may be described with reference to particular electronic devices, software architectures, networks, etc. However, those skilled in the art will recognize that the features are equally applicable to other electronic devices, software architectures, networks, etc. For example, while a computer program may be described as being implemented on a container, the computer program may be implemented on an electronic device that is communicatively connected to the container, or the computer program may be distributed amongst the container and electronic device. Accordingly, some tasks may be described as being performed by a container, while other tasks may be described as being performed by the electronic device. Those skilled in the art will recognize, however, that either the container or electronic device could perform many of these tasks.

Embodiments may also be described with reference to a container having a particular form. For example, several embodiments are described in the context of a cylindrical bottle having a cavity defined therein for storing a bulk supply of medication in the form of tablets. Those skilled in the art will recognize that these examples are provided for the purpose of illustration only. The technology could be implemented in other forms of medication packaging such as non-cylindrical containers, inhalers, syringes, blister packs, and the like.

While embodiments may be described in the context of computer-executable instructions, aspects of the technology can be implemented via hardware, firmware, or software. As an example, operations may be executed by a container to reduce the amount of power that is consumed over time. These operations may be tightly linked with hardware components that are housed in the container, so these operations may be embodied as firmware that is permanently programmed into read-only memory. For instance, a container may include firmware that, upon being executed by a processor, serves to ensure that one or more secondary switch assemblies are "turned on" only when a primary switch assembly generated a signal that indicates the cap has been removed from the structural body of the container.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" refers broadly to software components, firmware components, and/or hardware components. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Network-Connected Container Overview

Figure 1B:
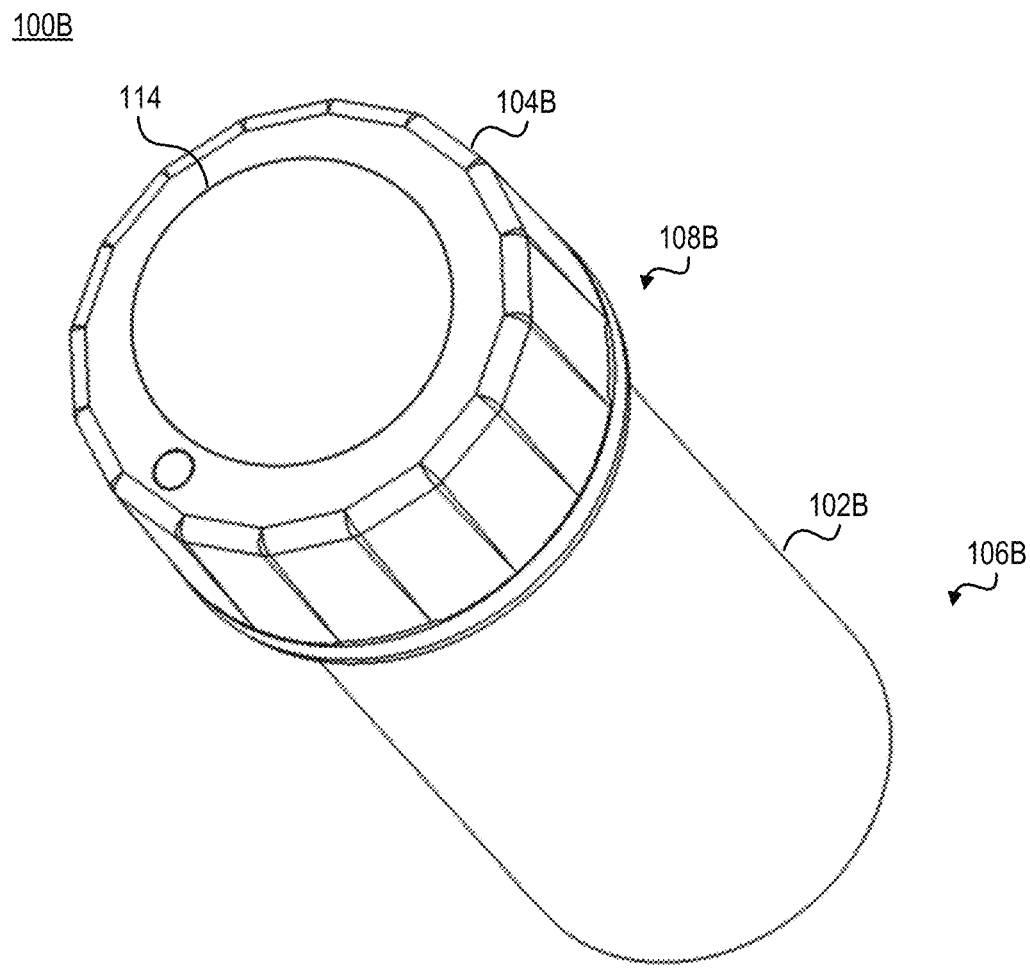

FIGS. 1A-B are perspective views of containers 100A-B with display units for conveying information regarding usage or the medication stored therein. In FIG. 1A, the information display unit is comprised of several illuminants located beneath an arcuate aperture 110 as further discussed below. In FIG. 1B, the information display unit is a display panel 114 comprised of light-emitting diodes (LEDs), organic LEDs, liquid crystal elements, or electrophoretic elements. In some embodiments, the display panel 114 may be touch sensitive. Thus, an individual may be able to provide input to the container 100B shown in FIG. 1B via the display panel 114. The information display units may be used to display the time elapsed since the containers 100A-B were last opened. Additionally or alternatively, the information display unit may be used to notify an individual when the medication that is stored therein is due to be administered.

The containers 100A-B have a durable housing. Generally, the durable housing includes a structural body 102A-B (also referred to as a "base") having a cavity defined therein for storing a bulk supply of medication and a cap 104A-B that is detachably connectable to the structural body 102A-B. When secured to the structural body 102A-B, the cap 104A-B encloses the cavity to retain the bulk supply of medication in the form of pills, power, aerosol, etc. Portions of the structural body 102A-B or cap 104A-B may be faceted or ribbed to improve the ease with which the containers 100A-B can be handled.

The structural body 102A-B may be in the form of a right circular hollow cylinder (also referred to as a "cylindrical shell") defined by a pair of right circular cylinders that share an axis in common and a base perpendicular to the common axis. The base may be located at a first end 106A-B (also referred to as the "distal end") of the cylindrical shell, and an aperture may be located at a second end 108A-B (also referred to as the "proximal end") of the cylindrical shell. In such embodiments, the second end 108A-B may be designed to accommodate the cap 104A-B. Those skilled in the art will recognize that hardware, firmware, and software components could be housed in either the structural body 102A-B or cap 104A-B. Accordingly, unless otherwise noted, the components described herein could be located in the structural body 102A-B or cap 104A-B.

As shown in FIGS. 1A-B, the container 100A-B includes an information display unit able to visually convey information, such as the time elapsed since the container was last opened or the time until the next administration of medication, to a user.

In FIG. 1A, the container 100A includes one or more illuminants that are located beneath an arcuate aperture 110 in the durable housing. The arcuate aperture 110 may be formed along the top of the cap 104A, or the arcuate aperture 110 may be formed along the side of the structural body 102A. These illuminant(s) can be driven to emit light to convey information regarding the medication stored therein.

As an example, a series of illuminants may be sequentially driven over time to visually convey information regarding usage of the container 100A. For instance, if the container 100A includes 6 illuminants, another illuminant may be driven every 2 hours to indicate when the container 100A was last opened. Thus, a first illuminant may be driven beginning 2 hours after the container 100A was last opened, a second illuminant may be driven beginning 4 hours after the container 100A was last opened, etc. As another example, a series of illuminants may be sequentially driven over time to visually convey information regarding the regimen. For instance, if the container 100A includes 6 illuminants and medication is to be administered every 12 hours, another illuminant may be driven every 2 hours to visually indicate when the next dose should be administered. In some embodiments each illuminant located beneath the arcuate aperture 110 is configured to emit light of the same color, while in other embodiments each illuminant located beneath the arcuate aperture 110 is configured to emit light of a different color.

In FIG. 1B, meanwhile, the container 100B includes a display panel 114 comprised of LEDs, organic LEDs, liquid crystal elements, or electrophoretic elements. The display panel 114 may be able to convey similar information as the LED(s) located beneath the arcuate aperture 110 shown in FIG. 1A. However, the display panel 114 may be able to present information in textual form. For example, the display panel 114 may present the actual time elapsed since the container 100B was last opened rather than an approximation of the time elapsed (e.g., where one illuminant is representative of at least two hours, two illuminants is representative of at least four hours, etc.). In some embodiments, the display panel 114 is touch sensitive. Thus, an individual may be able to provide input to the container 100B via the display panel 114.

In FIG. 1A, the cap 104A includes a tactile element 112 through which input can be provided. While not shown, the cap 104B shown in FIG. 1B could also include a tactile element. Accordingly, while the tactile element 112 may be discussed with reference to FIG. 1A, those skilled in the art will recognize that the tactile element 112 could be included in other embodiments of containers (e.g., those with display panels). Alternatively, another feature (e.g., the display panel 114) may be sensitive to touch, and therefore serve a similar purpose. To improve ease of use, some embodiments of the cap include a single centrally located tactile element 112 as shown in FIG. 1A. In other embodiments, the tactile element 112 is one of multiple tactile elements positioned along the exterior surface of the structural body 102A or cap 104A. In some embodiments, the tactile element 112 is representative of an actuator of a biased switch. For example, the tactile element 112 may be representative of the actuator of a normally-open (NO) switch that, when pressed, completed a circuit on a printed circuit board located in the cap 104A. Upon receiving an indication that the tactile element 112 has been pressed, the container 100A may infer that an action has been taken. For example, an individual may press the tactile element to activate the information display unit. As another example, an individual may be prompted to press the tactile element 112 to indicate that a dose of medication has been administered. As yet another example, an individual may be prompted to press the tactile element 112 as acknowledgement of a notification. As shown in FIG. 1A, the geometric center of the tactile element 112 may overlay the geometric center of the cap 104A. Here, for example, the midpoint of the substantially circular tactile element 112 overlays the midpoint of the substantially circular cap 104A. Since inadvertent interactions are more likely if the tactile element 112 is located along the side of the container 100A, the tactile element 112 may be located along the top surface of the cap 104A as shown in FIG. 1A.

Figure 2A:
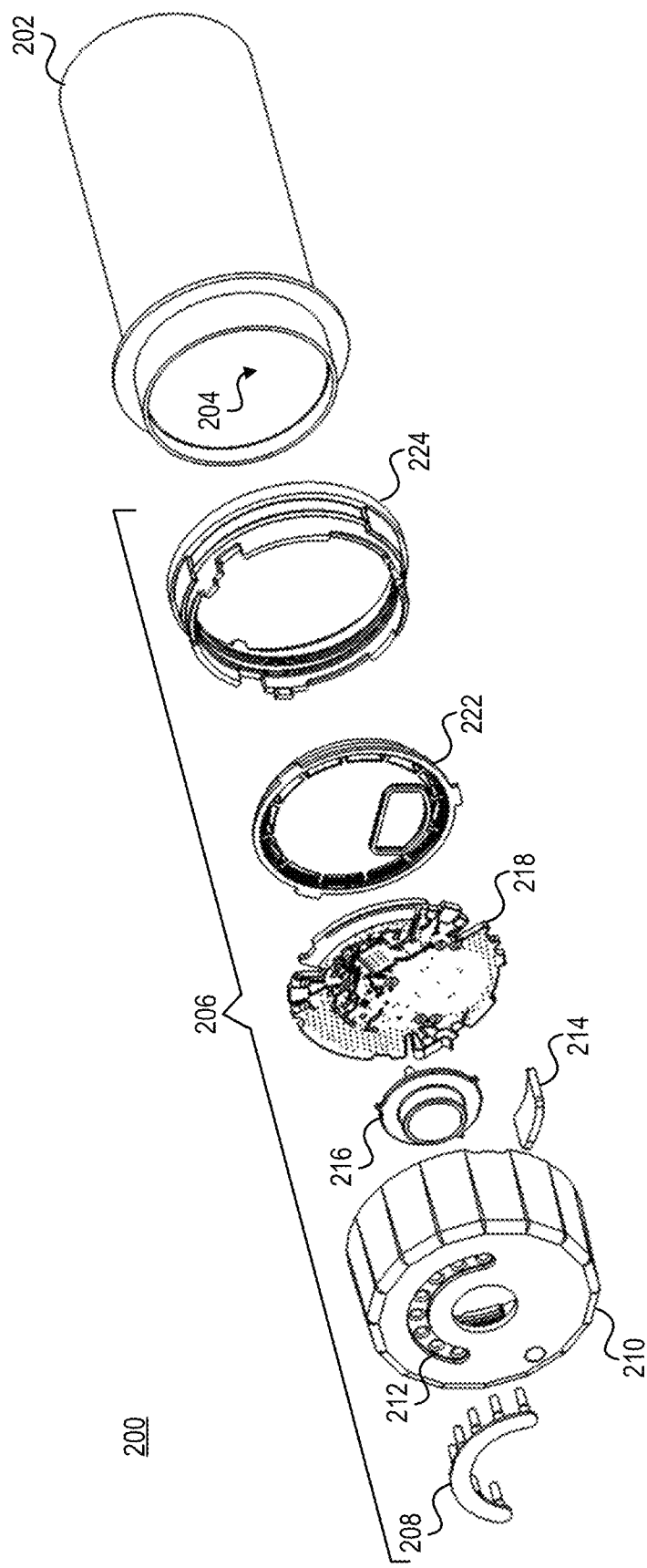
FIG. 2A is an exploded perspective view of a container that is able to indicate to an individual when the medication stored therein is due to be administered or when the container was last opened.
Figure 2B:
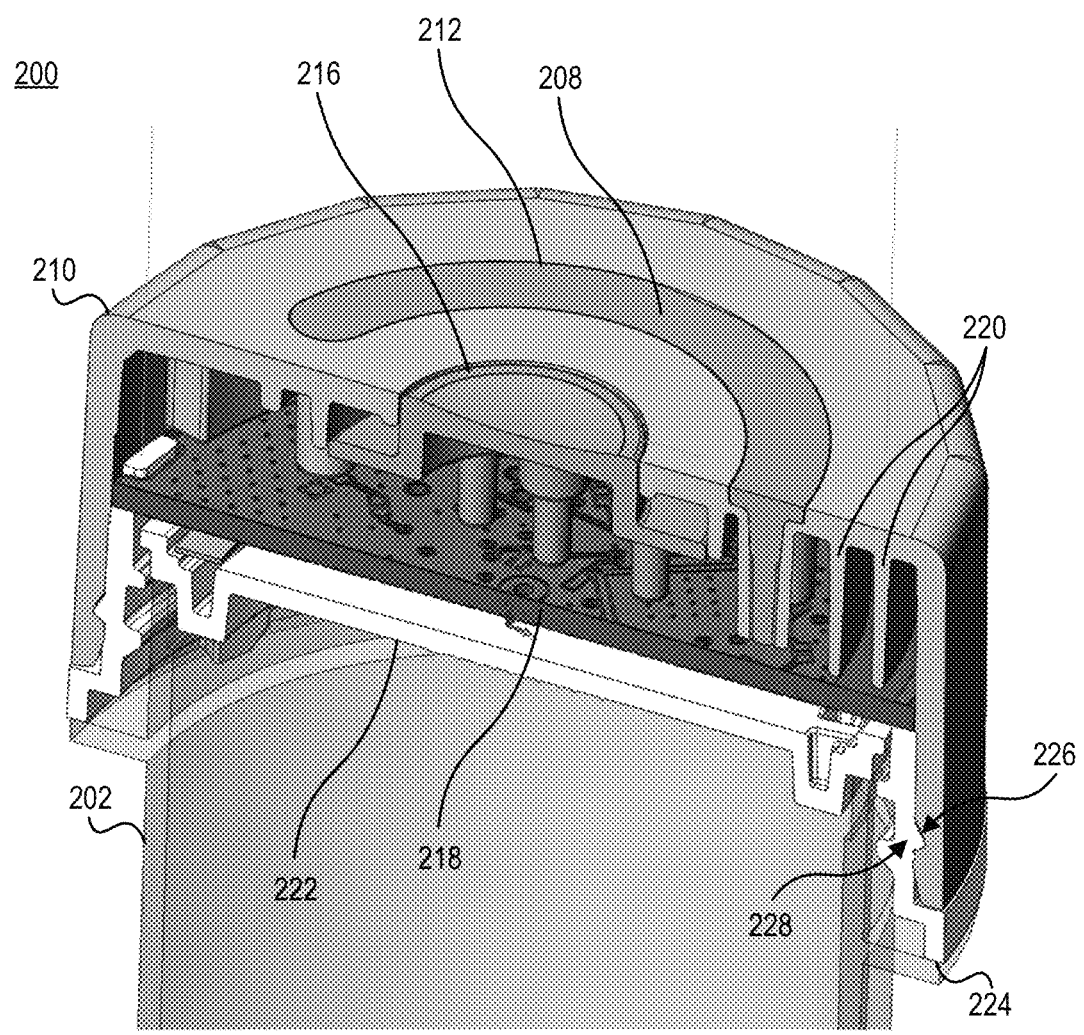
FIG. 2B is a cross-sectional perspective view of the container of FIG. 2A.

FIG. 2A is an exploded perspective view of a container 200 that is able to indicate to an individual when the container 200 was last opened. FIG. 2B, meanwhile, is a cross-sectional perspective view of the container 200 of FIG. 2A. The container 200 may be, for example, container 100 of FIG. 1. As discussed above, the container 200 has a durable housing that may be comprised of a structural body 202 having a cavity 204 defined therein for storing a bulk supply of medication and a cap 206 that is detachably connectable to the structural body 202.

The cap 206 may include a closure element 210 having an arcuate aperture 212 through which light can be emitted by illuminants that are mounted on a printed circuit board 218. These illuminants may be light-emitting diodes (LEDs). In some embodiments, a plurality of light guides configured to collimate the light emitted by the illuminants are arranged within the arcuate aperture 212. Each light guide has a proximal end that is located adjacent the corresponding illuminant and a distal end that is located adjacent the arcuate aperture 212. Each light guide may be comprised of a cylindrical structure having different diameters at the proximal and distal ends. Generally, these light guides are tapered with the diameter at the proximal end being smaller than the diameter at the distal end to promote the collimation of light. Furthermore, the first section of the light guide in the region near the proximal end may have an approximately parabolic change in diameter to further promote collimation of the light. The light guide may have a smooth surface to enhance total internal reflection of the light being emitted from the illuminant. The light guide may also be coated with a reflective layer such as a metal layer or a dielectric mirror. In some embodiments, the plurality of light guides are integrally formed as part of a unibody array 208 that is secured within the arcuate aperture 212 as a single unit. Here, for example, the closure element 210 includes a separate aperture for each light guide within the arcuate aperture 212, and the unibody array 208 can be positioned in the arcuate aperture 212 by sliding the light guides through the corresponding apertures.

The cap 206 may also have an aperture designed to accommodate a tactile element 216 for providing input. The tactile element 216 may be representative of an actuator of a biased switch that, when pressed, causes a circuit on the printed circuit board 218 to be completed, thereby generating a signal. The printed circuit board 218 may have various components mounted thereon. Examples of such components include processors, integrated circuits, illuminants, and the like. Moreover, the printed circuit board 218 may have tracks and/or vias that connect these components to one another, or that connect these components to other components such as antennas and fuses.

The printed circuit board 218 may have an upper surface and a lower surface opposite the upper surface that is oriented toward the cavity 204 in the structural body 202. To improve robustness of the container 200 against shaking, dropping, or jostling, one or more shock-absorbing elements 214 may be arranged orthogonal to the upper surface of the printed circuit board 218. At a high level, the shock-absorbing element(s) 214 can deform slightly in the event of a shock and serve to brace the printed circuit board 218 by absorbing some of the energy of the shock. The shock-absorbing element(s) 214 may also inhibit rattling of the printed circuit board 218, press plate 222, and support element 224. Generally, the cap 206 includes a plurality of shock-absorbing elements 214 that are spaced circumferentially about the printed circuit board 218. In such embodiments, the shock-absorbing elements 214 can be spaced radially about the printed circuit board 218 in an even spacing or an uneven spacing. The shock-absorbing element(s) 214 may be comprised of rubber, foam, or another elastic material. As shown in FIG. 2B, the closure element 210 may include a pair of structural features 220 that extend downward from the inner surface 210 toward the upper surface of the printed circuit board 218 to form a channel. Some or all of the shock-absorbing element(s) 214 may be contained within this channel.

A press plate 222 may be located beneath the printed circuit board 218. As shown in FIG. 2A, the press plate 222 may be a rigid annulus that floats within a gap between the printed circuit board 218 and the support element 224 that includes the structural features, such as threads or notches, which allow the cap 206 to be removably secured to the structural body 202.

The term "closing force," as used herein, refers to the force, torque, or moment applied to secure the cap 206 to the structural body 202 of the container 200. Said another way, the closing force will correspond to a closing motion representative of the cap 206 being secured to the structural body 202. Meanwhile, the term "opening force," as used herein, refers to the force, torque, or moment applied to remove the cap 206 from the structural body 202 of the container 200. When a closing force is applied to the cap 206, a force is created that causes the press plate 222 to move upward toward the switch assemblies mounted on the printed circuit board 218. More specifically, downward force applied to the top surface of the cap 206 (or upward force applied to the bottom surface of the structural body 202) may cause the press plate 222 to piston upward, thereby contacting the switch assemblies. The switch assemblies are further discussed below with reference to FIGS. 3A-B. In some embodiments, a malleable substrate (not shown) is positioned between the printed circuit board 218 and press plate 222. In such embodiments, the malleable substrate may be sufficiently elastic to deform as the press plate 222 moves upward toward the printed circuit board 218 and then regain its original shape as the press plate 222 moves downward away from the printed circuit board 218. To prevent unintentional contact with the switch assemblies, the thickness of the malleable substrate may be slightly larger than the height of the switch assemblies. Thus, the press plate 222 may need to partially deform the malleable substrate in order to contact the switch assemblies. The malleable substrate may be comprised of foam or another elastic material.

In some embodiments, components of the cap 206 are designed to be connected to one another via structural features and/or adhesives rather than screws. Here, for example, the closure element 210 includes a sunken feature 226 (also referred to as a "notch") while the support element 224 includes a protruding feature 228. The components in the cap 206 can be securably contained without adding screws by seating the protruding feature 228 in the sunken feature 226.

Figure 3A:
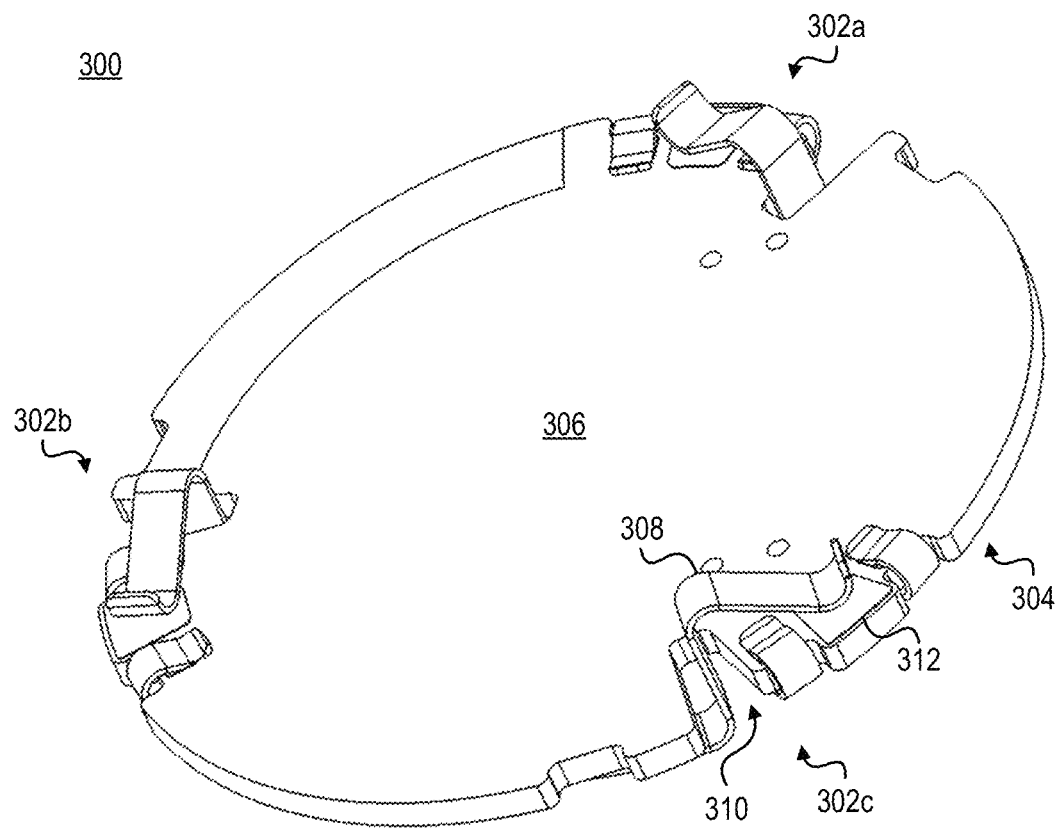
FIG. 3A is a top perspective view of a printed circuit board having a plurality of switch assemblies spaced circumferentially about the printed circuit board.

FIG. 3A is a top perspective view of a printed circuit board 300 having a plurality of switch assemblies 302a-c spaced circumferentially about the printed circuit board 300. These switch assemblies 302a-c may be spaced radially about the printed circuit board 300 in an even spacing or an uneven spacing. Here, three switch assemblies 302a-c are spaced radially about the printed circuit board 300 in an even spacing to form an equilateral triangle. However, embodiments of the printed circuit board 300 may include greater than three switch assemblies or fewer than three switch assemblies.

Each switch assembly 302a-c may include (i) a switch 308, (ii) an electrical contact 312 that generates a signal upon being contacted by the switch, and (iii) a resistor through which current is drawn when the switch contacts the electrical contact. Accordingly, the default state of each switch assembly 302a-c may be the "off state" where the switch naturally does not contact the electrical contact. Alternatively, the default state of each switch assembly 302a-c may be the "on state" where the switch naturally does contact the electrical contact. In such embodiments, the switch assemblies 302a-c can be designed/installed such that upward movement of the press plate (e.g., press plate 222 of FIG. 2) causes the switch to disconnect from the electrical contact, thereby interrupting the signal generated by the electrical contact. As further discussed below, each switch assembly 302a-c may also include an input/output (IO) pin through which current can be controllably provided to the resistor.

By examining the signals generated by the switch assemblies 302a-c, the container can determine whether changes in state have been experienced. For instance, the container may be configured to infer, based on the signals generated by the switch assemblies 302a-c, the cap was involved in an event. The term "event" may refer to removal of the cap from the structural body or installation of the cap on the structural body. As further discussed below, the container may determine whether the cap was involved in an event based on the signals generated by some or all of the switch assemblies 302a-c over a preceding interval of time. For example, the container may infer that an event occurred responsive to discovering that a signal was generated by each switch assembly over the preceding interval of time. As another example, the container may infer that an event occurred responsive to discovering that a signal was generated by a majority of the switch assemblies over the preceding interval of time. The preceding interval of time may be 100 milliseconds (ms), 300 ms, 500 ms, etc.

Figure 3B:
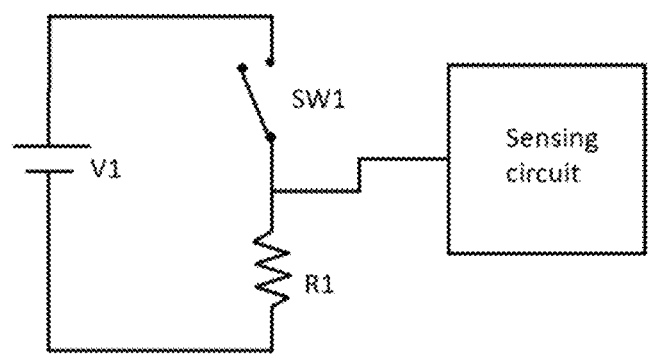
FIG. 3B includes a circuit diagram that illustrates how one of the switch assemblies shown in FIG. 3A could be connected in an electrical circuit to generate a signal as described.

The printed circuit board 300 has an upper surface 304 and a lower surface 306 opposite the upper surface that is oriented toward the cavity in which medication is stored. As shown in FIG. 3A, each switch 308 may be mounted along the upper surface 304 but extend beyond the lower surface 306 through an aperture 310 in the printed circuit board 300. Here, the aperture 310 is a notch along the perimeter of the printed circuit board 300, though the aperture 310 could take other forms. When the press plate adjacent the printed circuit board 300 moves upward, the press plate will apply force to the switch 308, thereby causing the switch 308 to break contact with the electrical contact 312. When the switch 308 breaks contact with the electrical contact 312, the electric potential or voltage of the electrical contact 312 will change from a high potential to a low potential. FIG. 3B includes a circuit diagram that illustrates how one of the switch assemblies shown in FIG. 3A could be connected in an electrical circuit to generate a signal as described.

Figure 4:
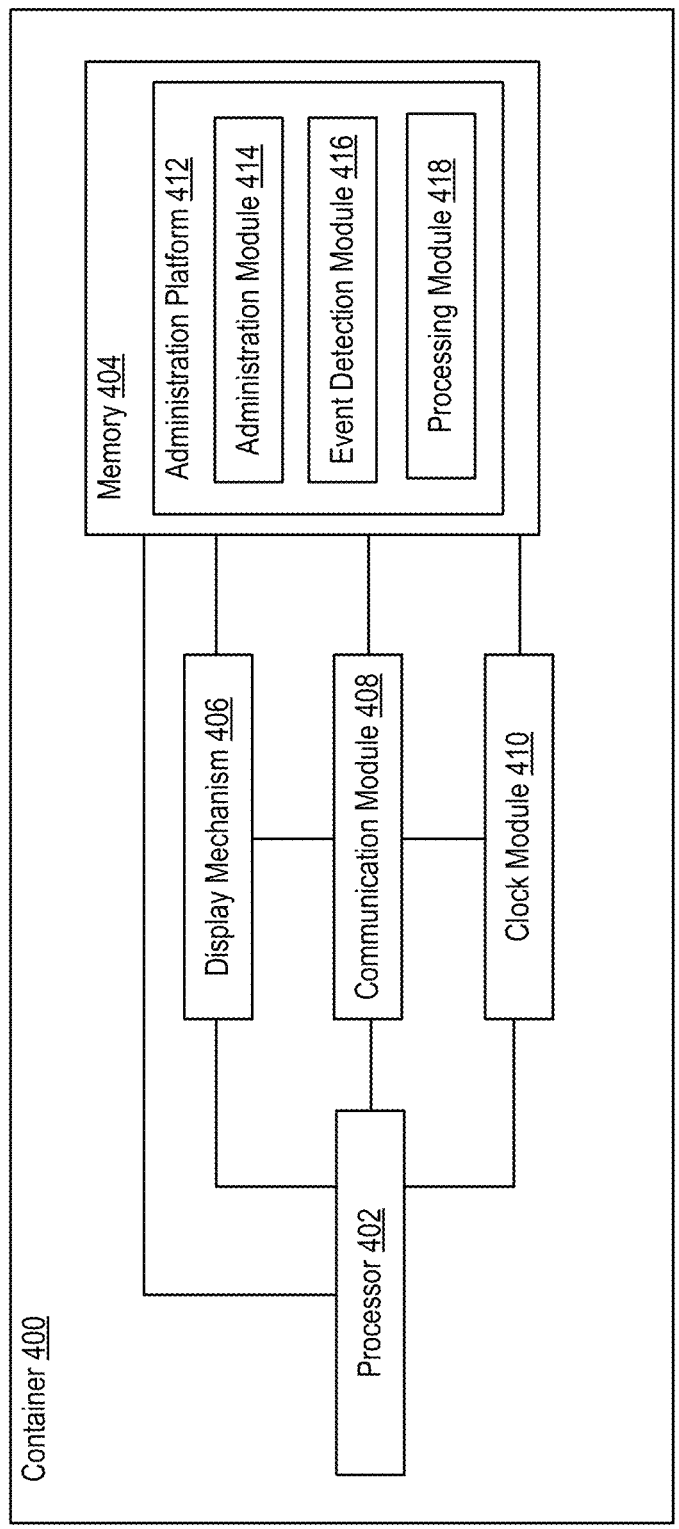
FIG. 4 illustrates an example of a container able to reliably assess whether an event involving the cap has occurred.

FIG. 4 illustrates an example of a container 400 able to reliably assess whether an event involving the cap has occurred. Such action enables administrations of medication to be more consistently and accurately inferred. By cataloguing events experienced by the cap of the container 400, an adherence platform can determine whether medication has been administered in compliance with a regimen.

In some embodiments, the adherence platform is embodied as a computer program that is executed by the container 400. In other embodiments, the adherence platform can be embodied as a computer program that is executed by an electronic device to which the container 400 is communicatively connected. In such embodiments, the container 400 may transmit data regarding administrations of medication to the electronic device for processing by the computer program as further discussed below. Those skilled in the art will recognize that the computer program could also be distributed amongst the container 400 and electronic device.

The container 400 can include a processor 402, memory 404, display mechanism 406, communication module 408, and clock module 410. The communication module 408 may be, for example, wireless communication circuitry designed to establish communication channels with other electronic devices. Examples of wireless communication circuitry include integrated circuits (also referred to as "chips") configured for Bluetooth®, Wi-Fi®, ZigBee®, LoRa®, Near Field Communication (NFC), and the like. The processor 402 can have generic characteristics similar to general-purpose processors, or the processor 402 may be an application-specific integrated circuit (ASIC) that provides control functions to the container 400. As shown in FIG. 4, the processor 402 can be coupled to all components of the container 400, either directly or indirectly, for communication purposes.

The memory 404 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 402, the memory 404 can also store data generated by the processor 402 (e.g., when executing the modules of the administration platform 412). Note that the memory 404 is merely an abstract representation of a storage environment. The memory 404 could be comprised of actual memory chips or modules.

The communication module 408 can manage communications between the components of the container 400. The communication module 408 can also manage communications with other electronic devices. For example, the administration platform 412 may reside, partially or entirely, on an electronic device to which the container 400 is communicatively connected as discussed above. Examples of electronic devices include mobile phones, tablet computers, and network-accessible server systems comprised of server(s). In such embodiments, the communication module 408 can transmit data generated by the container 400 to the electronic device for further analysis by the administration platform 412.

For convenience, the administration platform 412 may be referred to as a computer program that resides within the memory 404. However, the administration platform 412 could be comprised of software, firmware, and/or hardware components implemented in, or accessible to, the container 400. In accordance with embodiments described herein, the administration platform may include an administration module 414, event detection module 416, and processing module 418. These modules can be an integral part of the administration platform 412. Alternatively, these modules can be logically separate from the administration platform 412 but operate "alongside" it. Together, these modules may enable the administration platform 412 to discover when administrations of medication are likely to have occurred.

The clock module 410 is responsible for issuing a steady, high-frequency clock signal that can be used to determine whether a dose of medication is due to be administered. The clock module 410 may take the form of a chip that is mounted on the printed circuit board of the container 400.

The administration module 414 can be configured to examine a dosing schedule for the medication stored in the container 400 and then determine whether a dose is due to be administered based on a comparison of the dosing schedule and the clock signal generated by the clock module 410. More specifically, the administration module 414 can examine the dosing schedule to identify the times at which administration events are scheduled to occur and then determine, based on the clock signal, which administration events, if any, are due to be completed. In some embodiments the dosing schedule is stored in the memory 404, while in other embodiments the dosing schedule is stored in a remote memory accessible to the communication module 408 via a network.

If the administration module 414 determines that a dose of medication is due to be administered, the administration module 414 can cause a notification to be generated as an alert. More specifically, the administration module 414 can generate a signal for driving at least one indicator to produce the notification. Examples of indicators include speakers, feedback mechanisms, and display mechanisms. Thus, the container 400 may include a display mechanism 406 that is capable of visually conveying information. In some embodiments, the display mechanism 406 includes illuminant(s) that can be driven to emit light or change appearance on a periodic basis as a notification regarding what action, if any, should be taken with respect to the medication. Examples of illuminants include LEDs and organic LEDs. The components needed to operate the illuminant(s) may be connected to the illuminant(s) via conductive wires running through the container 400. Examples of operating components include drivers, processors (e.g., processor 402), and power sources such as batteries. While embodiments may be described in the context of illuminants, the technology is similarly applicable to other types of display mechanisms. For example, the container 400 may include reflective component(s) that create visual notifications by reflecting ambient light in addition to, or instead of, emissive components that create visual notifications by emitting light. Examples of reflective components include electrophoretic components and liquid crystal elements. Thus, the container 400 may include a display mechanism 406 that is configured to either emit or reflect light.

The event detection module 416 may be responsible for determining whether an event involving the cap of the container 400 has occurred based on signals generated by switch assemblies (e.g., switch assemblies 302a-c of FIG. 3A). As discussed above, these signals may indicate whether the switch assemblies have experienced a change in state. Since administrations events normally require that the cap be removed from the structural body, the event detection module 416 may infer whether administration events have occurred based on the presence, frequency, or timing of the signals generated by the switch assemblies. Said another way, the event detection module 416 may record that an administration event has occurred responsive to discovering that the switch assemblies experienced a change in state since changes in state are generally indicative of administration events. In other embodiments, the event detection module 416 may infer whether administration events occurred based on an analysis of movement data generated by an inertial measurement unit (IMU) that includes an accelerometer, gyroscope, etc. In other embodiments, the event detection module 416 may infer whether administration events occurred based on an analysis of tactile data representative of interactions with a tactile element of the container 400. For example, the event detection module 416 may be programmed to infer that interactions with a tactile element (e.g., tactile element 216 of FIG. 2) are representative of confirmations that administration events took place.

The processing module 414 may be responsible for applying operations to data obtained by the administration platform 412. As discussed above, the container 400 may produce data over time that indicates when doses of medication were administered. The processing module 414 may process (e.g., denoise, filter, or otherwise alter) this data so that it is usable by the other modules of the administration platform 412. Additionally or alternatively, the processing module 414 may be responsible for determining whether further action is necessary before this data is transmitted to the electronic device by the communication module 408. For example, the processing module 414 may assign priority measures to the data so that if bandwidth or power is limited, only the data deemed to be high priority is transmitted to the electronic device. As another example, the processing module 414 may filter the data to ensure that only relevant data (e.g., data concerning administrations of medication) is transmitted to the electronic device.

Figure 5:
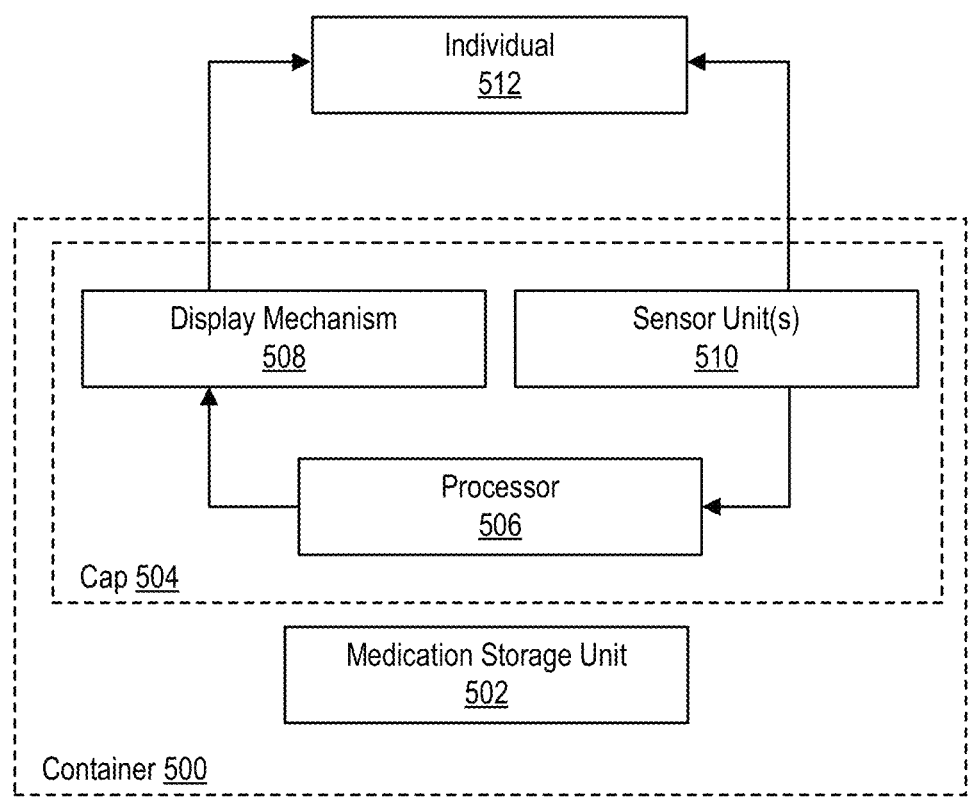
FIG. 5 includes a high-level system-level diagram of an embodiment of a container in which the processor, display mechanism, and sensor unit(s) are housed within the cap.

FIG. 5 includes a high-level system-level diagram of an embodiment of a container 500 in which the processor 506, display mechanism 508, and sensor unit(s) 510 are housed within the cap 504. One example of a sensor unit 510 is a switch assembly configured to generate signals from which occurrences of events involving the cap 504 can be inferred. Other examples of sensor units 510 include IMUs, pressure sensors, tactile elements, and the like.

In some embodiments, the display mechanism 508 includes a plurality of LEDs that, when driven by the processor 506, convey information regarding the time that has elapsed since the cap 504 was last removed and/or the time until the cap 504 should be next removed. Alternatively, the plurality of LEDs may convey information regarding the number of doses of medication remaining in the medication storage unit 502. In such embodiments, all of the LEDs may initially be driven by the processor 506. Then, as doses are administered by the patient 512, the LEDs may be sequentially turned off to visually indicate when more medication will be needed.

In some embodiments, the display mechanism 508 includes a plurality of independently operable displays capable of presenting different types of information. For instance, a first display may include a digital clock while a second display element may include information regarding the medication or container 500. As an example, the second display element may display the name of the medication or a color associated with the medication (e.g., on its packaging) to give the patient 512 confidence that the container 500 (and, more specifically, the dosing schedule implemented by the container 500) has been correctly matched with the medication stored therein. As another example, the second display element may display status indicators related to the container 500, such as power level, connectivity status, and the like.

In some embodiments, the display mechanism 508 is an "always on" display element capable of visually conveying information on a continual basis. One drawback of this approach, however, is that such display mechanisms may consume significant amounts of power over long intervals of time. One option for addressing this drawback is to ensure that the display mechanism 508 is only driven by the processor 506 when an individual 512 is nearby. The individual 512 may be, for example, the person to whom the medication has been prescribed, or another person responsible for assisting in administering the medication. The processor 506 may be able to establish proximity of the individual 512 in several different ways.

For example, the container 500 may include a microphone configured to generate data indicative of sounds external to its structural body. In such embodiments, the processor 506 may drive the display mechanism 508 only upon inferring, based on data generated by the microphone, that the individual 512 is likely within a given proximity. The inference may be based on the presence of a sound that is representative of the individual 512. For instance, the processor 506 may be able to detect keywords in the data, or the processor 506 may be able to identify an audible characteristic (e.g., frequency or cadence) that is representative of the individual 512.

As another example, the container 500 may include a proximity sensor configured to generate data representative of a series of proximity measurements indicative of proximity of the individual 512. The proximity sensor may emit an electromagnetic field or a beam of electromagnetic radiation (e.g., infrared radiation) and then look for changes in the electromagnetic field or return beam of electromagnetic radiation. In such embodiments, the processor 506 may drive the display mechanism 508 only upon inferring, based on the data, that the individual 512 is within a given proximity.

As another example, the container 500 may include an accelerometer configured to generate data representative of a series of measurements of acceleration of the container 500. In such embodiments, the processor 506 may drive the display mechanism 508 only upon inferring, based on the data, that the individual 512 has interacted with the container 500 within a given amount of time. The inference may be based on at least one acceleration measurement that exceeds a predetermined value or a series of acceleration measurements that match a pattern-defining parameter.

As another example, the container 500 may include a tactile element (e.g., tactile element 216 of FIG. 2) that is accessible through its durable housing. Data indicative of events involving interactions with the tactile element can be generated by, for example, a pressure sensor or electrical contact positioned beneath the tactile element. In such embodiments, the processor 506 may drive the display mechanism 508 only upon determining, based on the data, that the individual 512 has interacted with the tactile element within a given amount of time.

As another example, the container 500 may include a communication module configured to communicate with an electronic device associated with the individual 512. For instance, the container 500 may include a Bluetooth Low Energy chipset or a Wi-Fi chipset. In such embodiments, the processor 506 may drive the display mechanism 508 only upon inferring that the patient 512 is within a given proximity. Such an inference may be based on whether the communication module is presently able to establish a communication channel with the electronic device.

While the examples provided above concern controlling the display mechanism 508 in a less power-intensive manner, similar approaches may be employed to intelligently drive or manage other components of the container 500. For example, to conserve power, the processor 506 may activate sensors (e.g., infrared sensors, acoustic sensors, accelerometers, gyroscopes) housed in the container 500 only upon inferring that the patient 512 is nearby.

Figure 6:
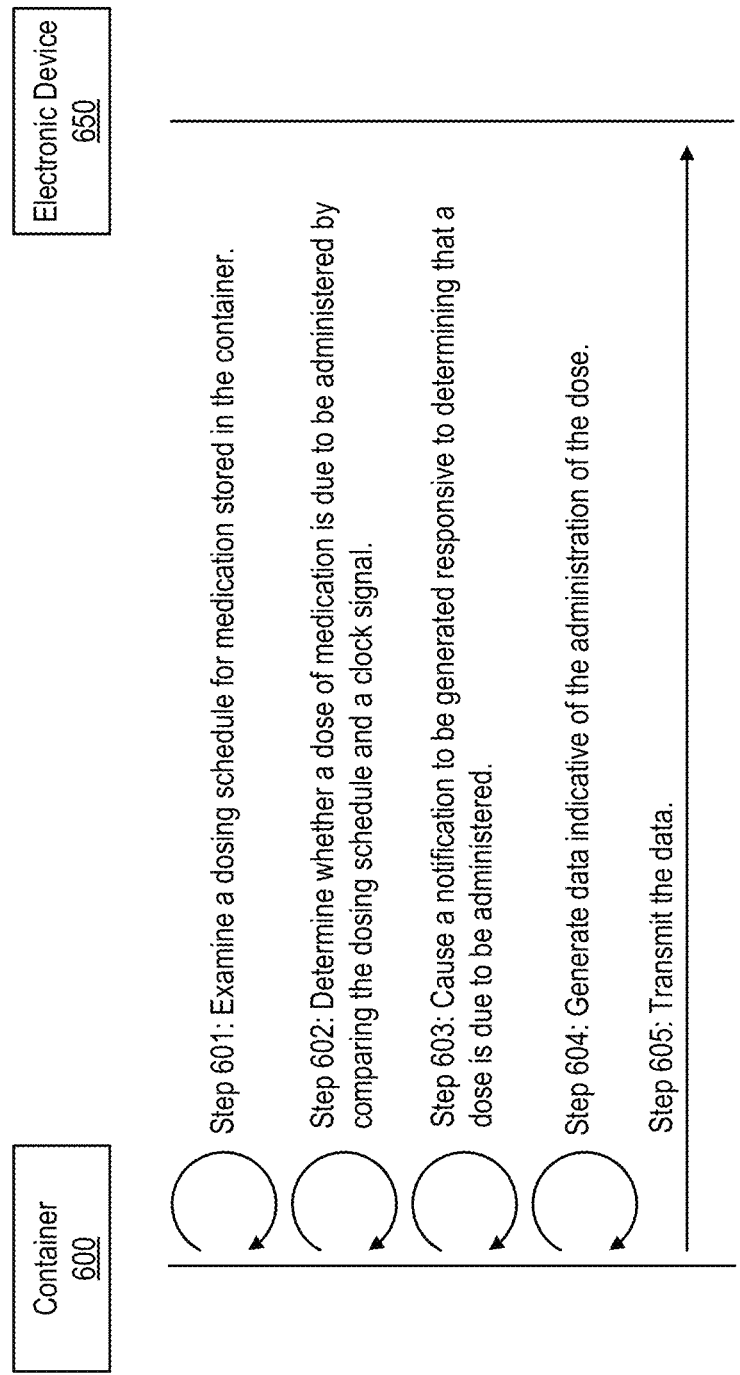
FIG. 6 includes a high-level illustration of communications between a container that includes a bulk supply of medication and an electronic device that is responsible for processing, examining, or forwarding data related to administrations of the medication so that compliance with a regimen can be determined.

FIG. 6 includes a high-level illustration of communications between a container 600 (e.g., container 200 of FIGS. 2A-B or container 400 of FIG. 4) that includes a bulk supply of medication and an electronic device 650 that is responsible for processing, examining, or forwarding data related to administrations of the medication so that compliance with a regimen can be determined. One example of an electronic device 650 is a mobile phone associated with the person to whom the medication has been prescribed. Another example of an electronic device is a docking unit or hub unit configured to forward the data to a computer server of a network-accessible server system for analysis.

Initially, the container 600 can examine a dosing schedule for a medication stored therein (step 601). In some embodiments, the dosing schedule is manually loaded into local memory. For example, a medical professional or the person to whom the medication has been prescribed may input the dosing schedule through a computer program executing on the electronic device 650, and the computer program may forward the dosing schedule to the container 600. In other embodiments, the dosing schedule is automatically retrieved from a remote memory during a configuration process. For example, the dosing schedule may be retrieved from a network-accessible storage medium associated with a medical enterprise such as a hospital or pharmacy when the medication is loaded into the container 600.

Then, the container 600 can determine whether a dose of medication is due to be administered by comparing the dosing schedule and a clock signal generated by a clock module (step 602). In response to determining that a dose of medication is due to be administered, the container 600 can cause a notification to be generated by an indicator (step 603). Examples of indicators include illuminants operable to produce visual notifications, speakers operable to produce audible notifications, and feedback mechanisms operable to produce tactile notifications. In some embodiments, the notification is generated on a periodic basis. For example, the container 600 may drive an illuminant such that light is emitted (e.g., by flashing or pulsing) on a periodic basis as a visual notification.

The container 600 may be able to generate data indicative of administrations of doses of medication (step 604). This administration data may be useful in determining the degree of compliance with a regimen requiring administration of the medication. For example, the administration data may provide insights into the compliance of individual administration events (e.g., whether a scheduled dose was skipped) or series of administration events (e.g., whether scheduled doses are routinely administered late).

This administration data may comprise, or be derived from, various types of data generated by components of the container 600. For example, the container 600 may infer that administration events have occurred based on an analysis of signals generated by switch assemblies contained within the cap. As another example, the container 600 may infer that administration events have occurred based on an analysis of data generated by an IMU whose movement is representative of movement of the container 600. As another example, the container 600 may infer that administration events have occurred based on an analysis of data generated by a pressure sensor located beneath the cavity in which medication is stored. As another example, the container 600 may infer that administration events have occurred based on an analysis of data representative of interactions with a tactile element accessible along the outer surface of the container 600.

The container 600 may transmit at least some of the administration data to the electronic device 600 for analysis (step 605). For example, a processor responsible for processing the administration data may forward this data to a transmitter for modulation onto an antenna for wireless transmission to the electronic device 650. The transmitter may be part of a transceiver capable of transmitting communications to, and receiving communications from, the electronic device 650. Step 605 may be performed whenever the container 600 and electronic device 650 are communicatively connected to one another. For example, if the container 600 and electronic device 650 are configured to communicate with one another via a short-range communication protocol, step 605 may be performed whenever the electronic device 650 is within sufficient proximity of the container 600 to communicate via the short-range communication protocol.

Other steps could also be performed by the container 600 and/or electronic device 650. For example, the electronic device 650 may be responsible for transmitting information regarding the regimen to the container 600 for implementation. Said another way, the electronic device 650 may transmit information regarding when doses are to be administered to the container 600, and then the container 600 may store this information for use in determining when doses are due to be administered.

Note that, in some embodiments, the container 600 may be designed in such a manner to ensure the cap has been placed on the corresponding structural body. As one example, the cap and corresponding structural body may be color coded as a matching set. Thus, the cap and corresponding structural body may have a given color affixed thereto to indicate the relationship. As another example, the cap and corresponding structural body may be pattern coded as a matching set. For instance, the cap and corresponding structural body may have matching patterns imprinted thereon to indicate the relationship.

Communication Environment

Figure 7:
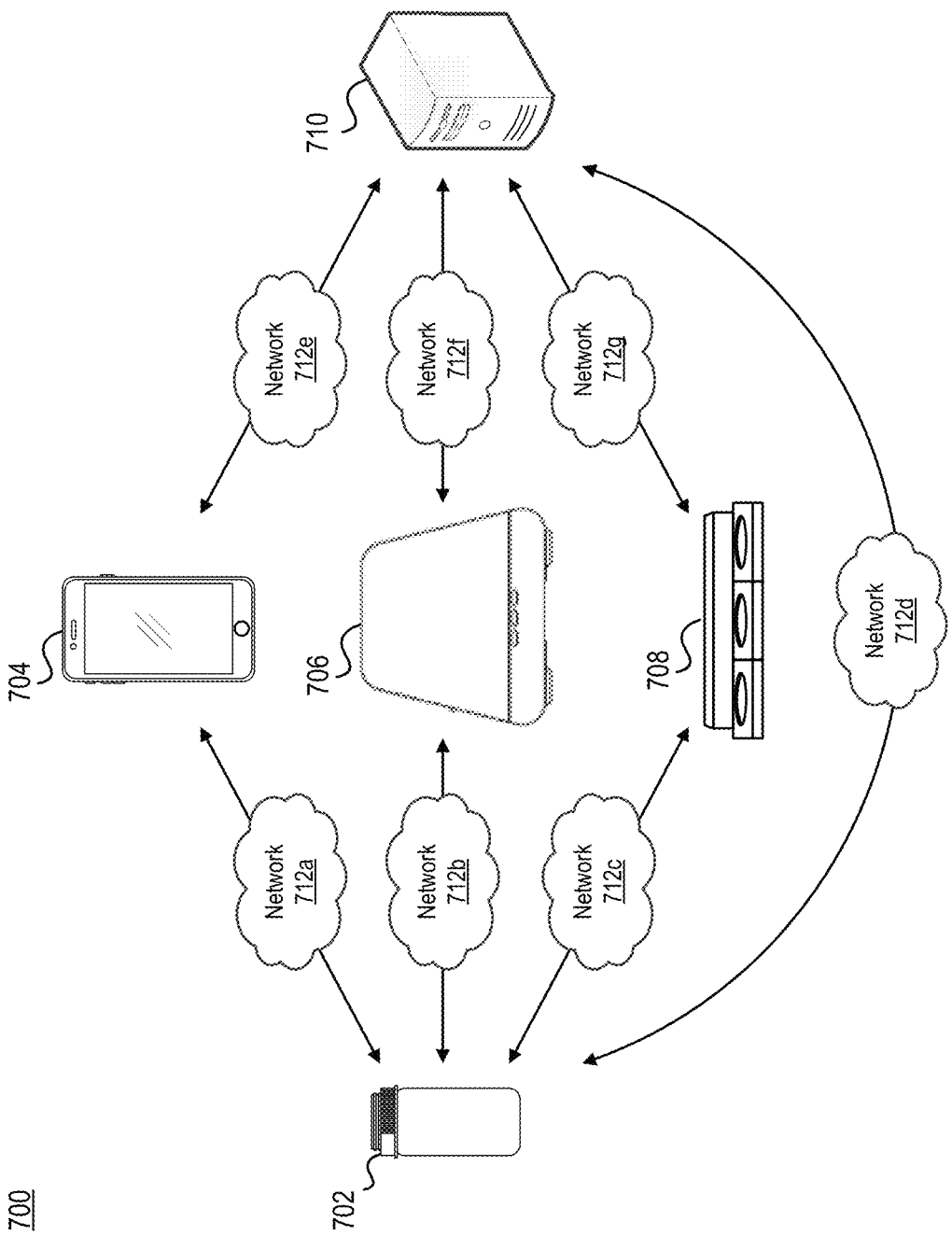
FIG. 7 depicts an example of a communication environment that includes a container having medication stored therein.

FIG. 7 depicts an example of a communication environment 700 that includes a container 702 having medication stored therein. As discussed above, the container 702 can be configured to communicate with one or more electronic devices. For example, the container 702 may transmit data related to administrations of the medication to an electronic device for further analysis. Examples of electronic devices include mobile phones 704, hub units 706, docking units 708, and computer servers 710. The container 702 and electronic device(s) may collectively be referred to as the "networked devices."

The networked devices can be connected to one another via one or more networks 712*a-g*. The network(s) 712*a-g* can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth, NFC, Wi-Fi, ZigBee, LoRa, another commercial point-to-point protocol, or a proprietary point-to-point protocol. For example, the container 702 may include a Bluetooth Low Energy chipset or a Wi-Fi chipset that establishes a wireless communication channel with the mobile phone 704, which is communicatively coupled to the computer server 710 via a Wi-Fi communication channel or a cellular communication channel.

Embodiments of the communication environment 700 may include some or all of the networked devices. For example, some embodiments of the communication environment 700 include the container 702 and a single electronic device (e.g., the mobile phone 704) that is responsible for analyzing data generated by the container 702. As another example, some embodiments of the communication environment 700 include the container 702 and a computer server 710 on which data generated by the container 702 is stored for subsequent analysis. Further information on networked containers can be found in U.S. Provisional Application No. 62/962,784, titled "Networked Containers Designed to Promote Compliance with a Medication Regimen," which is incorporated by reference herein in its entirety.

Multi-Assembly Event Detection to Increase Redundancy

As discussed above in reference to FIG. 3A, a plurality of switch assemblies may be spaced circumferentially about a cap of a container. The cap may be removed from the container by several methods, for example, by unscrewing via threaded features, popping off, pressing-and-turning, and other methods known in the art. The removal of the cap from the container will allow a press plate located adjacent to the plurality of switch assemblies to move, and the movement of the press plate will change the force that is applied to the plurality of switches. As an example, to remove the cap from the structural body of a container, an individual may apply an upward force to the cap and/or a downward force to the structural body. This causes downward movement of the press plate relative to the PCBA on which the plurality of switch assemblies are mounted. The downward movement will relieve pressure on the plurality of switch assemblies, thereby allowing the switch assemblies to contact the corresponding electrical contacts and generate a signal. Alternatively, the downward movement may cause the switch assemblies to break contact with the corresponding electrical contacts, thereby causing a signal to be interrupted. Thus, each switch assembly may be configured to either open or close an electrical connection due to changes in force, and this signal could be detected by a sensing circuit as shown in FIG. 3B.

By examining the signals generated by the plurality of switch assemblies, the container can infer whether an event involving the cap occurred. More specifically, the container may implement an algorithm—in software or firmware—that considers changes in state as detected by each switch assembly when inferring whether an event occurred. As noted above, the term "event" may refer to removal of the cap from the structural body or installation of the cap on the structural body. Such an approach allows the container to filter invalid events that could be caused by mechanical bouncing of the switches in the switch assemblies, partial engagement of the cap with the structural body, transient changes in state caused by impact force (e.g., from dropping, shaking, or jostling), or incidental user interactions (e.g., fidgeting with the cap).

Figure 8:
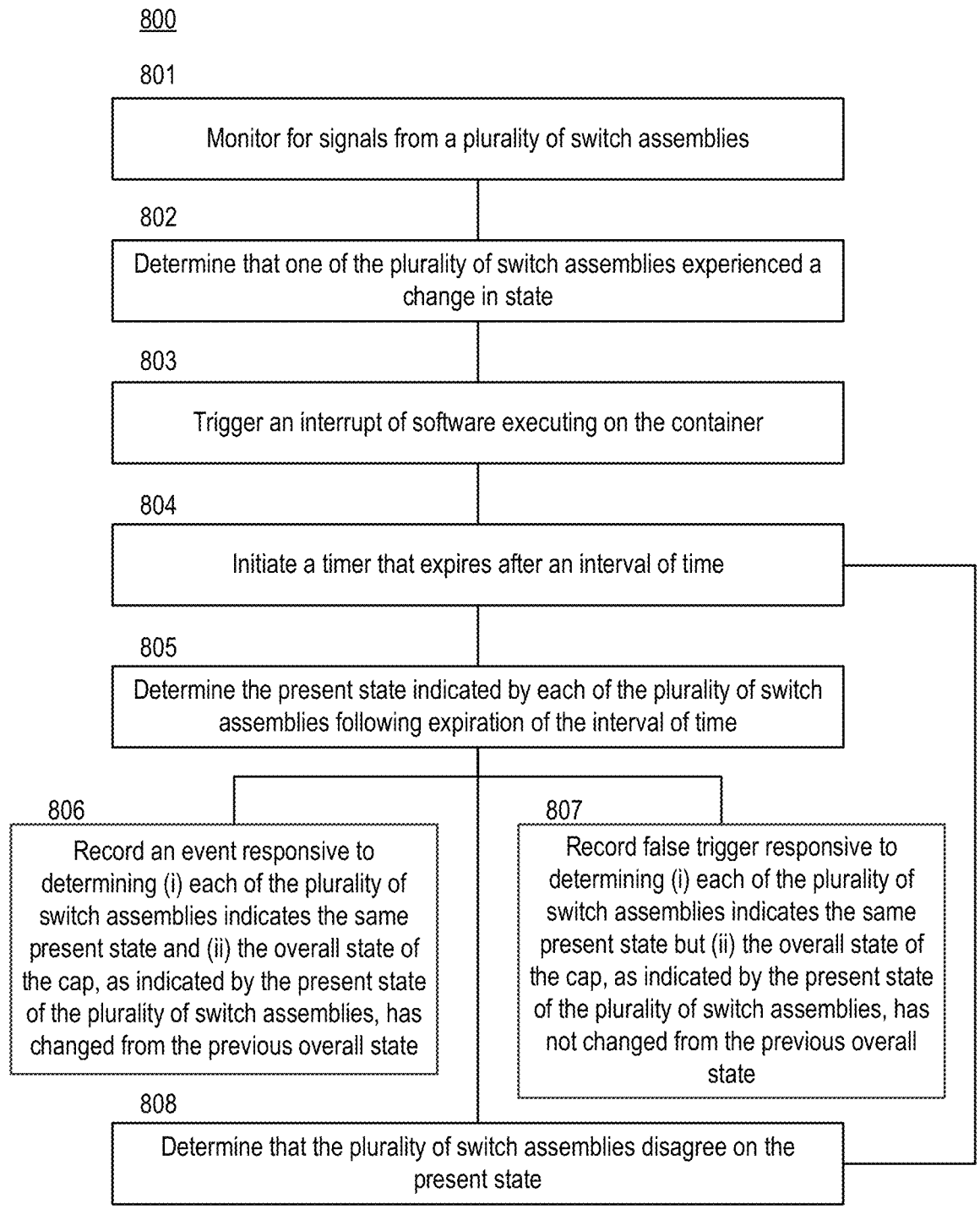
FIG. 8 includes a flow diagram of a process for determining whether an event involving a cap has occurred based on changes in state experienced by a plurality of switch assemblies.

FIG. 8 includes a flow diagram of a process 800 for determining whether an event involving a cap has occurred based on changes in state experienced by a plurality of switch assemblies. Initially, a processor can monitor for signals from the plurality of switch assemblies that are spaced circumferentially about a perimeter of a cap (step 801). As shown in FIG. 3A, the plurality of switch assemblies may be spaced circumferentially about a printed circuit board on which the processor is mounted. Thereafter, the processor may determine that one of the plurality of switch assemblies experienced a change in state (step 802). Such a determination may be made upon receiving a signal from that switch assembly indicating that its switch contacted its electrical contact if it was previously not in contact, or that its switch broke contact with its electrical contact if it was previously in contact. For example, the processor may determine that the signal generated by one of the plurality of switch assemblies indicates that the cap has been removed (i.e., changed from an "on state" to an "off state") or attached (i.e., changed from an "off state" to an "on state").

Upon receiving the signal, the processor can trigger an interrupt of the software executing on the container (step 803), subsequently initiating a timer that expires after an interval of time (step 804). The interval of time may have a predetermined duration that is based on typical bounce characteristics of switch assemblies. Generally, the interval of time is roughly 150 ms, 100 ms, or 75 ms in duration, though the duration may be adjusted empirically based on, for example, the number of false negatives or false positives discovered while performing the process 800. For instance, if the processor discovers that false negatives occur at more than a predetermined frequency, then the processor may shorten the interval of time.

When the interval of time expires, the processor can determine the present state indicated by each of the plurality of switch assemblies (step 805). The processor can record that an event occurred responsive to determining that (i) each of the plurality of switch assemblies indicates the same present state and (ii) the overall state of the cap, as indicated by the present state of each of the switch assemblies, has changed from the previous overall state (step 806). That is, an event can be recorded if the plurality of switch assemblies agree on the present state and the present state is different from the previously recorded state. If the plurality of switch assemblies have the same present state but this state is the same as that previously recorded, then the processor may record a false trigger (step 807). Alternatively, the processor may simply ignore false triggers.

If the processor discovers that the plurality of switch assemblies disagree on the present state (step 808), then the processor can initiate a confirmation operation in which steps 804-805 are repeated one or more times. For example, these steps may be repeated five times to establish the actual state. If the plurality of switch assemblies do not agree after completing the confirmation operation, the processor can record the disagreement so that further action can be taken. For example, the individual responsible for administering the medication may be notified. As another example, information regarding the disagreement may be transmitted to another electronic device (e.g., a computer server) for troubleshooting of the container.

Approaches to Reducing Power Consumption

Managing power may be critical to ensuring that containers described herein can be used over the course of several days, weeks, or months. As such, operations may be executed by these containers to reduce the amount of power that is consumed over time. Examples of such operations are described below with reference to FIGS. 9-12. Because these operations are tightly linked with the hardware components contained in the containers, these operations may be embodied as firmware that is permanently programmed into read-only memory. Alternatively, these operations may be executable aspects of an administration platform (e.g., administration platform 412 of FIG. 4).

Figure 9:
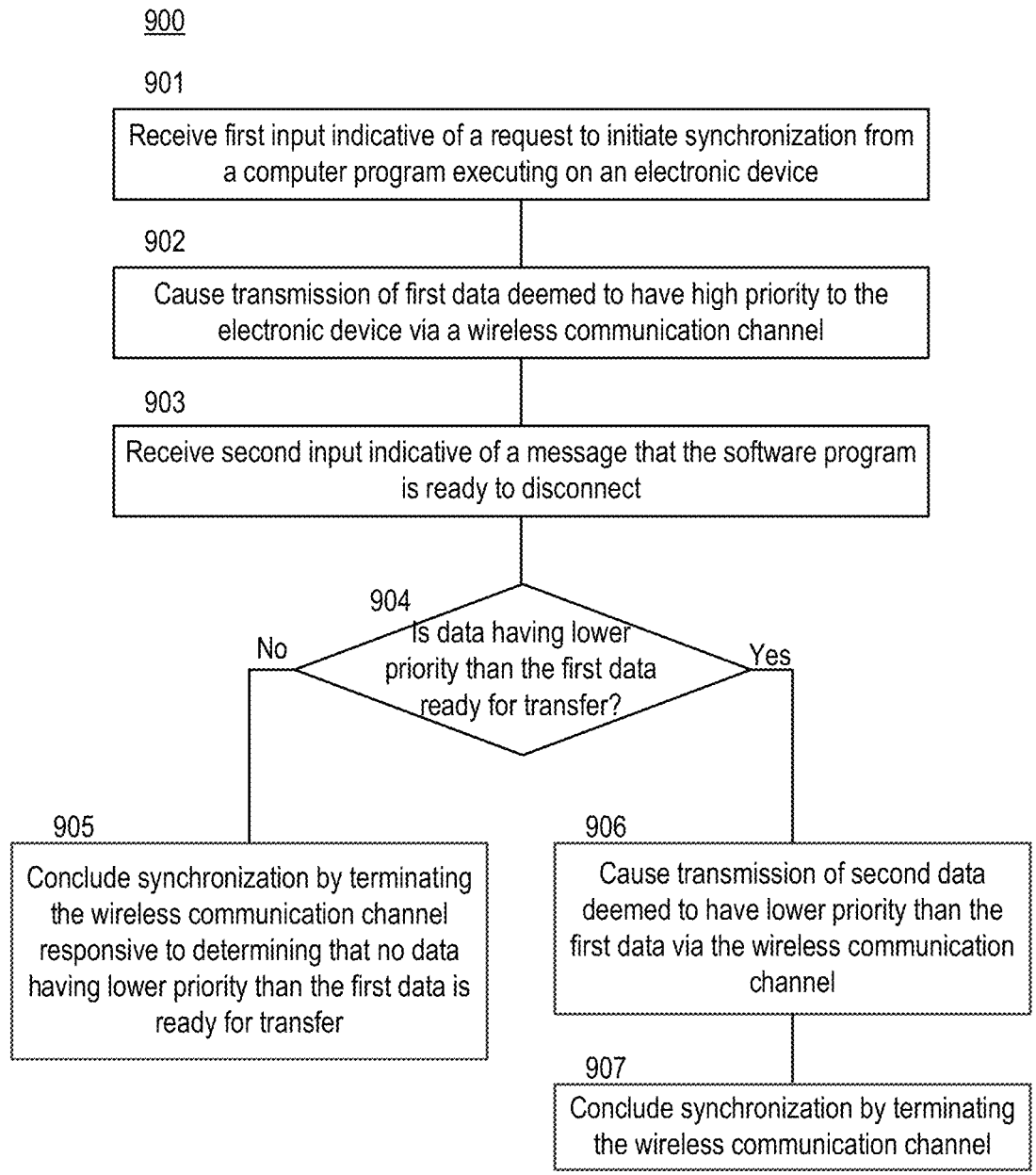
FIG. 9 includes a flow diagram of a process for implementing an automated process (also referred to as a "handshake") for transferring data between a container and a computer program executing on an electronic device in a more efficient manner.

FIG. 9 includes a flow diagram of a process 900 for implementing an automated process (also referred to as a "handshake") for transferring data between a container and a computer program executing on an electronic device in a more efficient manner. Generally, data is transferred between the container and computer program through a request-response pattern in which the computer program sends a request message to the container and the container responds with a response message. Because the amount of power available to the container is limited, it may be desirable to limit the number of exchanges (also referred to as "synchronization events" or "synchronization sessions") that occur.

Some data that is generated by the container may be low priority. Low priority data may be data unrelated to administrations of medication (e.g., data related to diagnostics or usage), or spurious enough that the data need not be requested during every synchronization (e.g., data related to errors, such as those experienced by the switch assemblies). One example of low-priority data is data identifying false triggers (e.g., discovered by performing process 800 of FIG. 8). Since this low-priority data is not needed to establish whether medication was administered in accordance with a regimen, it can be transmitted to the computer program less frequently. Accordingly, rather than the computer program requesting the same type(s) of data during each synchronization event, the computer program may instead request that any high-priority data generated since the previous synchronization event be transmitted and then send a confirmation message indicating that it is ready to disconnect. The container can send low-priority data upon receiving the confirmation message, or the container can simply disconnect if there is no low-priority data to send. Performing this final handshake during each synchronization event enables power to be saved where there is no low-priority data to send.

As shown in FIG. 9, the container may initially receive first input indicative of a request to initiate synchronization from a computer program executing on an electronic device (step 901). The computer program may be designed to promote adherence to a dosing schedule for medication stored in the container. For example, the computer program may be configured to analyze data regarding administrations of medication that was generated by the container to determine whether the medication was administered in accordance with a dosing schedule. Similarly, the computer program may be configured to analyze data regarding administrations of medication to establish how much medication resides in the container. In some embodiments requests to initiate synchronization are received from the computer program on a periodic basis, while in other embodiments requests to initiate synchronization are received from the computer program on an ad hoc basis. For example, the computer program may transmit a request to initiate synchronization whenever communication with the container is possible over a short-range communication protocol. Thus, requests to initiate synchronization may be transmitted by the computer program whenever the container and electronic device are within proximity of one another.

Alternatively, the container may be responsible for determining when synchronization with the computer program can occur. For example, the container may be configured to locally broadcast signals in accordance with a short-range communication protocol to determine whether synchronization can occur. One example of a short-range communication protocol over which synchronization can be performed is Bluetooth. These signals may be representative of advertising signals that are broadcast periodically (e.g., every 60 minutes, 90 minutes, or 120 minutes) or on an ad hoc basis (e.g., whenever an event occurs). Thus, the computer program may only send a request to initiate synchronization responsive to receiving an advertising signal from the container.

Thereafter, the container may cause transmission of first data deemed to have high priority to the electronic device via a wireless communication channel (step 902). Priority may be determined based on priority measures assigned different types of data by the computer program. For example, the computer program may indicate that data regarding administrations of medication (also referred to as "administration data") is high priority while data regarding status (e.g., power level, connectivity state, and amount of remaining medication) is lower priority.

As discussed above, the container can then receive a second input indicative of a message that the computer program is ready to disconnect (step 903). This second input may be representative of a request to complete synchronization by terminating the wireless communication channel established between the container and electronic device. Upon receiving the second input, the container can determine whether data having lower priority than the first data is ready for transfer (step 904). In some instances, the container will determine that no data having lower priority than the first data is ready for transfer, and the container can simply conclude synchronization by terminating the wireless communication channel (step 905). In other instances, the container will determine that data having lower priority than the first data is ready for transfer. In such instances, the container can cause transmission of second data having lower priority than the first data (step 906) and then conclude synchronization by terminating the wireless communication channel (step 907).

Those skilled in the art will recognize that the process 900 will differ depending on whether low-priority data is ready for transfer. Over an extended period of time (e.g., several hours or days), the computer program may transmit a series of requests to initiate synchronization to the container. Some exchanges may conclude following transmission of high-priority data, while other exchanges may conclude following transmission of high- and low-priority data. Each of these exchanges may occur over a separate instance of a wireless communication established in accordance with, for example, a short-range communication protocol such as Bluetooth.

To secure data prior to transmission to the computer program, the container may implement an encryption scheme. Some encryption schemes provide for an initial pairing of the container and computer program using a shared code or password and then involve a power-intensive sequence of exchanges and cryptographic computations. To lessen the amount of power that is consumed over time, the container may instead use a master key that is stored during the initial pairing to restore communications with the computer program during subsequent synchronization events. Such an approach enables the container to quickly initiate a secure connection with the computer program in a manner that requires fewer exchanges and cryptographic computations (and thus less power).

Figure 10:
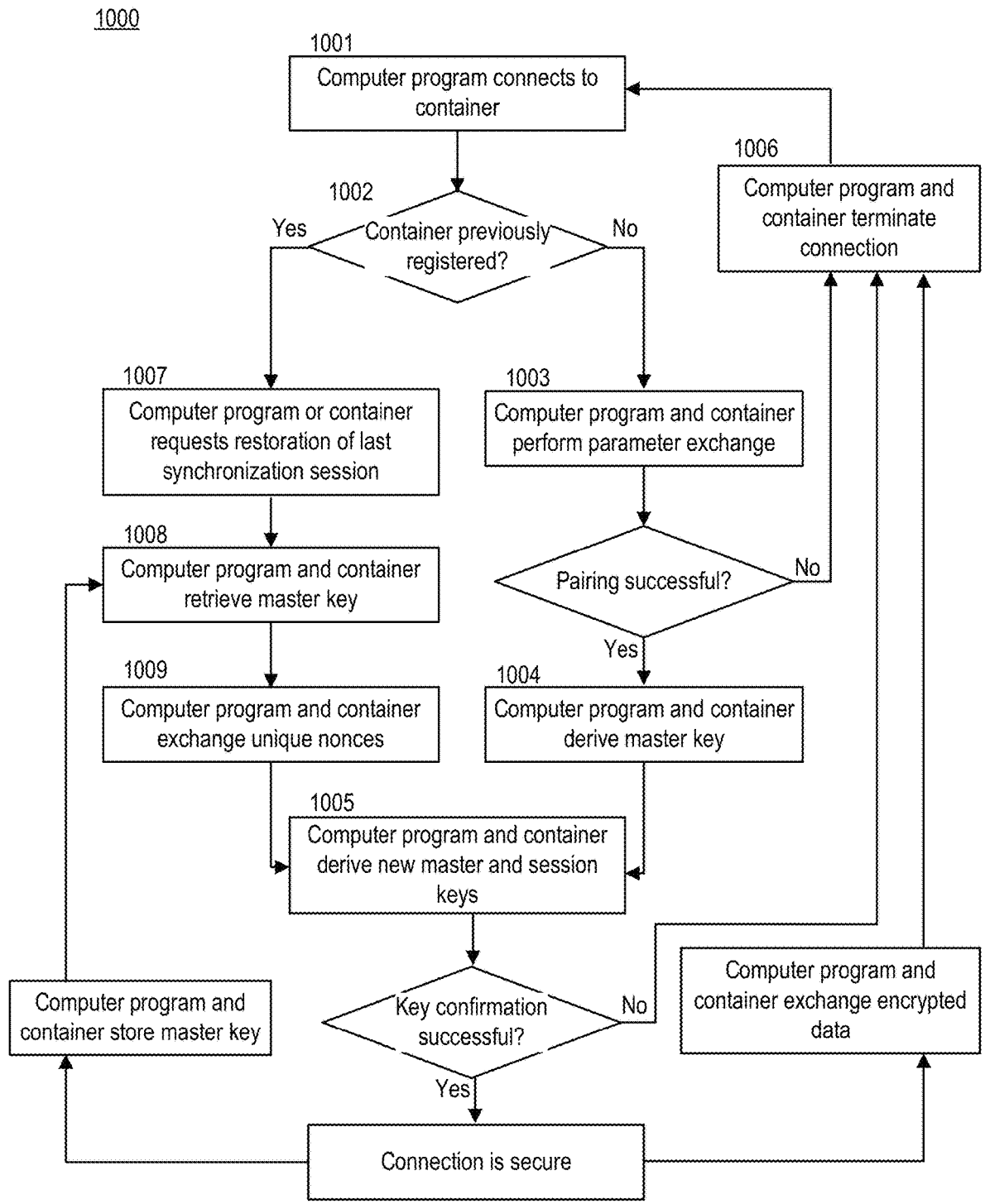
FIG. 10 includes a flow diagram of a process for implementing an encryption scheme that ensures data transferred between a container and a computer program executing on an electronic device remains secure.

FIG. 10 includes a flow diagram of a process 1000 for implementing an encryption scheme that ensures data transferred between a container and a computer program executing on an electronic device remains secure. Initially, the computer program can connect to the container (step 1001). In some embodiments, the computer program causes the electronic device to broadcast an identifier that is detectable by the container. In other embodiments, the computer program instructs the electronic device to monitor for an identifier broadcast by the container. For example, the container may be configured to periodically broadcast an identifier over a short-range communication protocol that is detectable by the electronic device. Upon discovering the container, the computer program can determine whether the container was previously registered in accordance with the encryption scheme (step 1002).

If the container was not previously registered, the computer program and container can perform an exchange of cryptographic parameters (step 1003). If the exchange is successful, the computer program and container can derive a shared master key (step 1004) and then derive session keys (step 1005). Successful confirmation of the master and session keys ensures that the connection between the computer program and container is secure. If the confirmation is not successful, the computer program can terminate the connection with the container (step 1006) and then reinitiate the process 1000.

If the container was previously registered, then the computer program or container can request restoration of the last synchronization session (step 1007). Then, the computer program and container can retrieve the master key that was derived during the initial synchronization session (step 1008) and then exchange unique nonces (step 1009). If the exchange is successful, the computer program and container can derive a new master key and session keys (step 1005) based on the retrieved master key and unique nonces in order to establish a secure connection as discussed above. The new master key can be saved for subsequent executions of this step in future connections.

By implementing the process 1000 of FIG. 10, some cryptographic calculations can be avoided following the initial pairing. Such an approach ensures that the computer program and container can quickly establish a secure connection in a less power-intensive manner.

Figure 11:
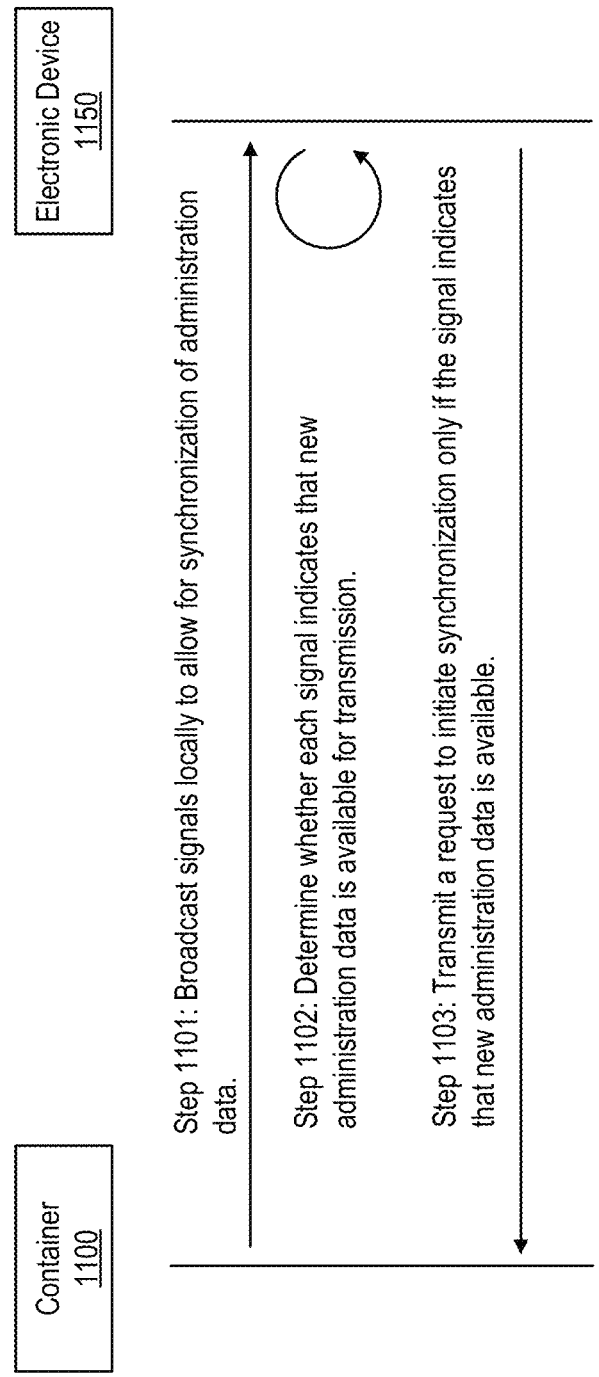
FIG. 11 includes a flow diagram of a process for performing an abbreviated synchronization event to conserve power.

FIG. 11 includes a flow diagram of a process for performing an abbreviated synchronization event to conserve power. As discussed above, a container 1100 may be configured to transmit data regarding administrations of medication to an electronic device 1150 for further analysis. Generally, administration data is periodically transmitted from the container 1100 to the electronic device 1150 as part of a synchronization event. Because each synchronization event involves an exchange of messages between the container 1100 and electronic device 1150, completing the synchronization event will require that power be consumed by the container 1100 and electronic device 1150. By implementing the process of FIG. 11, however, synchronization events can be avoided when the container 1100 does not have new administration data available for transmission to the electronic device 1150.

Over time, the container 1100 may locally broadcast signals to allow for synchronization of administration data stored thereon (step 1101). These signals may be broadcast periodically (e.g., once every 15 minutes, 30 minutes, or 60 minutes) regardless of whether there is new data to be transmitted to the electronic device 1150 or whether the electronic device 1150 is presently within proximity of the container 1100. Generally, these signals are broadcast by the container 1100 in accordance with a short-range communication protocol. For example, these signals may be representative of advertising signals that are broadcast by the container 1100 over Bluetooth.

To reduce the number of unnecessary synchronization events, the container 1100 may place a label (also referred to as a "flag") in each signal that indicates whether new administration data has been generated since the most recent transfer of administration data to the electronic device 1150. Accordingly, for each signal that is received, the electronic device 1150 may determine whether the signal indicates that new administration data is available for transmission from the container 1100 (step 1102). More specifically, the electronic device 1150 may parse each signal to discover whether a flag is present that indicates new administration data is available. The electronic device 1150 may transmit a request to initiate synchronization only if the signal indicates that new administration data is available (step 1103). Accordingly, the electronic device 1150 may choose to initiate synchronization only when new administration data is available, thereby allowing the container 1100 and electronic device 1150 to save power that would be required to complete synchronization. Note, however, that the electronic device 1150 may register that a synchronization event occurred whenever a signal is received. Thus, the electronic device 1150 may register that a synchronization event occurred regardless of whether new administration data was actually obtained from the container 1100.

In some embodiments, the flag only indicates whether new high-priority data is available. For example, the flag may be used to indicate whether high-priority data such as administration data has been generated since the most recent synchronization event. In other embodiments, the flag indicates whether new high- or low-priority data is available. As discussed above, priority may be based on priority measures assigned different types of data by an administration platform executing on the container 1100 and/or electronic device 1150. If all of the new data is low priority, then the electronic device 1150 may opt against a transfer of such data until new high-priority data is available.

Alternatively, the container 1100 may be configured to not broadcast any signals unless new administration data is available. Such an approach will cause even less power to be consumed than the process of FIG. 11, though it may come at the expense of the electronic device 1150 losing the ability to establish whether the container 1100 is within range. For example, the signals broadcast by the container 1100 may also include information regarding its state, such as power level and connectivity status, in addition to the flag. If the signals are not broadcast unless new data is available, the electronic device 1150 may not be able to accurately establish status of the container 1100.

Another option for conserving power is deactivating some hardware components of the container when those hardware components are not needed. FIG. 12 includes a flow diagram of a process 1200 for controllably activating and then deactivating a plurality of switch assemblies configured to generate signals from which events involving the cap of a container can be inferred. As discussed above with reference to FIG. 3A, each switch assembly can include a switch, an electrical contact that generates a signal upon being contacted by the switch or by breaking contact with the switch, a resistor through which current is drawn when the switch contacts the electrical contact, and an IO pin through which a bias voltage can be supplied to the resistor. To lessen the amount of power needed by the container, at least some of the switch assemblies can be "turned off" by applying the appropriate bias voltage to their resistors through the corresponding IO pins.

More specifically, the container can identify a primary switch assembly from amongst the plurality of switch assemblies (step 1201) and all switch assemblies other than the primary switch assembly as secondary switch assemblies (step 1202). Then, the container can cause the appropriate bias voltage to be supplied to the resistor of each secondary switch assembly via the corresponding IO pin (step 1203). Such an approach causes the secondary switch assemblies to be "turned off." When a secondary switch assembly is "turned off," it will not draw current through its resistor or be responsive to changes in state.

Thereafter, the container can monitor for signals from the primary switch assembly (step 1204) and then determine whether the cap has experienced a change in state based on the signals generated by the primary switch assembly (step 1205). Upon determining that the signals generated by the primary switch assembly indicate a change in state, the container may cause a change in the appropriate bias voltage to be supplied to the resistor of each secondary switch assembly via the corresponding IO pin. Such action will cause the secondary switch assemblies to be "turned on." When a secondary switch assembly is "turned on," it will be responsive to changes in state.

The container can then establish whether the cap truly experienced a change in state based on the signals generated by the primary switch assembly and signals generated by the secondary switch assemblies. For example, the container may confirm that the secondary switch assemblies are in the same present state as the primary switch assembly, in which case the container can infer that an event involving the cap did truly occur. Then, the container can cause an appropriate "turn on" bias voltage to be provided to the resistor of each secondary switch assembly via the corresponding IO pin once again. Thus, the secondary switch assemblies can be "turned on" when the primary switch assembly detects a change in state and then "turned off" after agreement between the primary and secondary switch assemblies has been found.

In some embodiments, the primary switch assembly is randomly identified from amongst the plurality of switch assemblies. Alternatively, the primary switch assembly may be identified from amongst the plurality of switch assemblies on a rotating basis. In some embodiments, the primary switch assembly is identified from amongst the plurality of switch assemblies on a periodic basis. For example, the container may select a primary switch assembly from amongst the plurality of switch assemblies every 3 hours, 12 hours, 24 hours, etc. As another example, the container may select a primary switch assembly whenever a scheduled synchronization event with the electronic device is completed. In other embodiments, the primary switch assembly is identified from amongst the plurality of switch assemblies on an ad hoc basis. For example, assume that the container discovers the primary switch assembly has experienced a malfunction, such as a mechanical fault or electrical fault. In such embodiments, the container may ensure that signals, if any, received from the primary switch assembly are no longer considered when determining whether the cap has experienced a change in state. Instead, the container may determine whether an event has occurred based on a consensus on present state between the secondary switch assemblies, one of which may be selected as the new primary switch assembly.

Processing System

Figure 13:
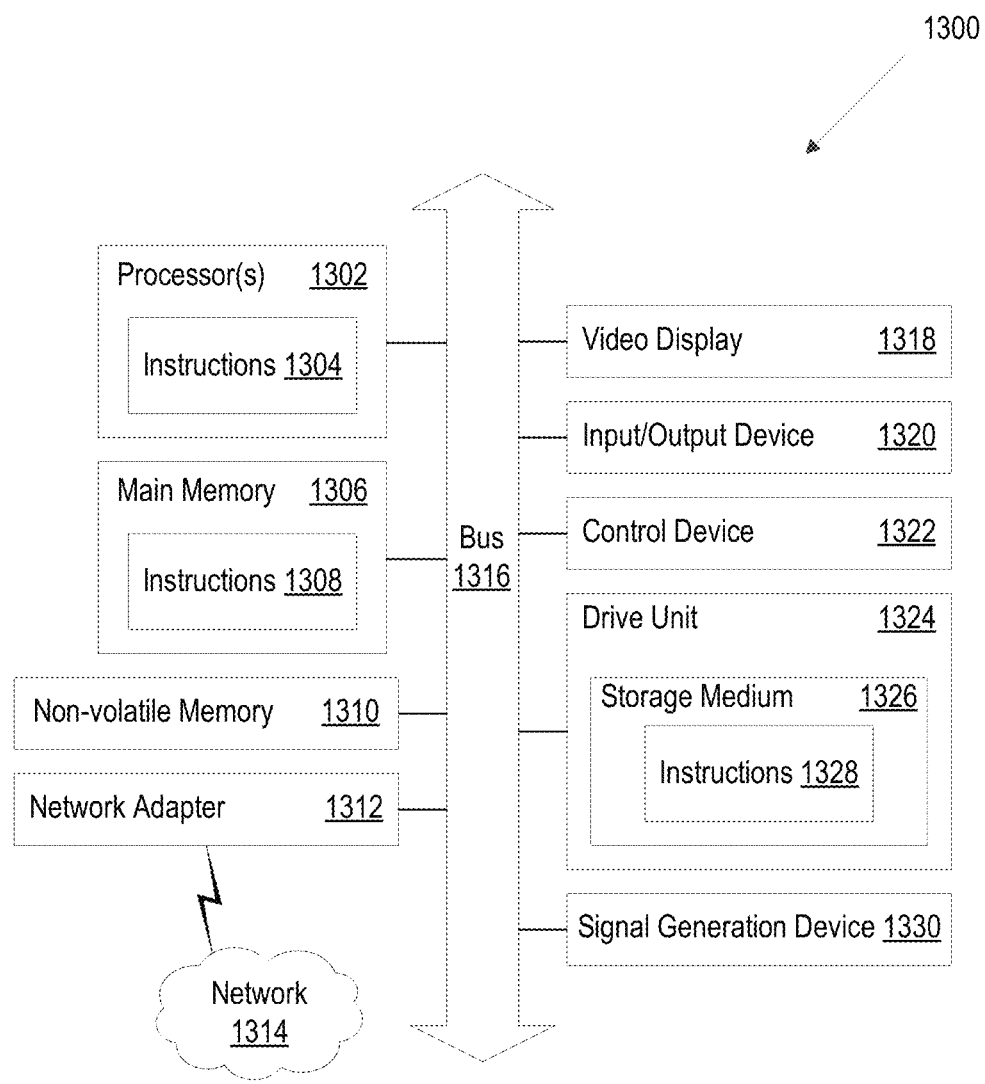
FIG. 13 is a block diagram illustrating an example of a processing system in which at least some operations described herein can be implemented.

FIG. 13 is a block diagram illustrating an example of a processing system 1300 in which at least some operations described herein can be implemented. For example, some components of the processing system 1300 may be hosted on a container (e.g., container 100 of FIG. 1, container 200 of FIGS. 2A-B, or container 400 of FIG. 4). As another example, some components of the processing system 1300 may be hosted on an electronic device that is connected to a container across a network.

The processing system 1300 may include one or more central processing units ("processors") 1302, main memory 1306, non-volatile memory 1310, network adapter 1312 (e.g., a network interface), video display 1318, input/output devices 1320, control device 1322 (e.g., a keyboard or pointing device), drive unit 1324 including a storage medium 1326, and signal generation device 1330 that are communicatively connected to a bus 1316. The bus 1316 is illustrated as an abstraction that represents one or more physical buses or point-to-point connections that are connected by appropriate bridges, adapters, or controllers. The bus 1316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC ($I^2C$) bus, or an Institute of Electrical and Electronics Engineers (IEEE) standard 1394 bus (also referred to as "Firewire").

The processing system 1300 may share a similar processor architecture as that of a desktop computer, tablet computer, mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1300.

While the main memory 1306, non-volatile memory 1310, and storage medium 1326 are shown to be a single medium, the terms "machine-readable medium" and "storage medium" should be taken to include a single medium or multiple media (e.g., a centralized/distributed database and/or associated caches and servers) that store one or more sets of instructions 1328. The terms "machine-readable medium" and "storage medium" shall also be taken to include any medium that is capable of storing, encoding, or carrying a set of instructions for execution by the processing system 1300.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1304, 1308, 1328) set at various times in various memory and storage devices in an electronic device. When read and executed by the processors 1302, the instruction(s) cause the processing system 1300 to perform operations to execute elements involving the various aspects of the present disclosure.

Moreover, while embodiments have been described in the context of fully functioning electronic devices, those skilled in the art will appreciate that some aspects of the technology are capable of being distributed as a program product in a variety of forms. The present disclosure applies regardless of the particular type of machine- or computer-readable media used to effect distribution.

Further examples of machine- and computer-readable media include recordable-type media, such as volatile and non-volatile memory devices 1110, removable disks, hard disk drives, and optical disks (e.g., Compact Disk Read-Only Memory (CD-ROMS) and Digital Versatile Disks (DVDs)), and transmission-type media, such as digital and analog communication links.

The network adapter 1312 enables the processing system 1300 to mediate data in a network 1314 with an entity that is external to the processing system 1300 through any communication protocol supported by the processing system 1300 and the external entity. The network adapter 1312 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

The network adapter 1312 may include a firewall that governs and/or manages permission to access/proxy data in a network. The firewall may also track varying levels of trust between different machines and/or applications. The firewall can be any number of modules having any combination of hardware, firmware, or software components able to enforce a predetermined set of access rights between a set of machines and applications, machines and machines, or applications and applications (e.g., to regulate the flow of traffic and resource sharing between these entities). The firewall may additionally manage and/or have access to an access control list that details permissions including the access and operation rights of an object by an individual, a machine, or an application, and the circumstances under which the permission rights stand.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method performed by a container in which medication is stored, the method comprising:
   broadcasting a signal in accordance with a short-range communication protocol to indicate willingness to perform synchronization;
   receiving first input that is indicative of a response to the signal from a computer program executing on an electronic device,
      wherein the computer program is designed to promote adherence to a regimen that requires administration of the medication;
   causing transmission of first data deemed to have high priority to the electronic device via a first wireless communication channel;
   receiving second input that is indicative of a request to complete synchronization from the computer program;
   determining that no data having lower priority than the first data is ready for transmission to the computer program; and
   concluding synchronization by terminating the first wireless communication channel.

2. The method of claim 1, further comprising:
   receiving third input that is indicative of a request to initiate synchronization from the computer program;
   causing transmission of second data deemed to have high priority to the electronic device via a second wireless communication channel;
   receiving fourth input that is indicative of a request to complete synchronization from the computer program;
   determining that third data having lower priority than the second data is ready for transmission to the computer program;
   causing transmission of the third data deemed to have low priority to the electronic device via the second wireless communication channel; and
   concluding synchronization by terminating the second wireless communication channel.

3. The method of claim 1, wherein priority is determined based on priority measures assigned to different types of data by the computer program.

4. The method of claim 1, wherein the first wireless communication channel is initiated in accordance with the short-range communication protocol.

5. The method of claim 1, wherein the signal is one of multiple signals broadcast by the container in accordance with the short-range communication protocol on a periodic basis.

6. The method of claim 1, wherein the short-range communication protocol is the Bluetooth communication protocol.

7. The method of claim 1, wherein requests to initiate synchronization are received by the container on an ad hoc basis.

8. The method of claim 1, wherein the computer program is a mobile application, and wherein the electronic device is a mobile phone that is associated with an individual to whom the medication is prescribed.

9. A non-transitory medium with instructions stored thereon that, when executed by a processor, cause the processor to perform operations comprising:
   receiving a plurality of signals that are locally broadcast by a container having medication stored therein over an interval of time;
   for each of the plurality of signals,
      determining whether the signal indicates that new data regarding administrations of the medication is available for download from the container; and
      in response to a determination that the signal indicates that new data is available,
         transmitting, to the container, a first request to initiate a wireless communication channel over which data is transferrable,
         receiving, from the container, the new data via the wireless communication channel, and
         transmitting, to the container, a second request to prompt termination of the wireless communication channel and complete synchronization.

10. The non-transitory medium of claim 9, wherein said determining involves parsing the signal to discover whether a flag is present that indicates new data regarding administrations of the medication has been generated since a most recent transmission of data regarding administrations of the medication from the container.

11. The non-transitory medium of claim 9, wherein the wireless communication channel is established in accordance with a short-range communication protocol.

12. The non-transitory medium of claim 9, wherein the plurality of signals are representative of advertising signals that are periodically broadcast by the container over a wireless personal area network.

13. The non-transitory medium of claim 9, wherein the operations further comprise:
   registering an event indicating that synchronization occurred whenever one of the plurality of signals is received.

14. A container comprising:
   a structural body having a cavity defined therein for storing a bulk supply of medication;
   memory in which data having different levels of priority is stored;
   communication circuitry that is configured to locally broadcast signals on a periodic basis to indicate willingness to perform synchronization; and
   a processor that is configured to, in response to receiving a response to one of the signals from an electronic device that is proximate to the container:
      cause transmission of at least some of the data deemed to have high priority to the electronic device via a wireless communication channel established by the communication circuitry,
      receive input that is indicative of a request to complete synchronization from the electronic device,
      determine that no data having lower priority is ready for transmission to the electronic device, and
      conclude synchronization by terminating the wireless communication channel.

15. The container of claim 14, wherein the processor is further configured to assign measures indicative of priority to the data, so that the data is transmittable to the electronic device in decreasing order of priority.

16. The container of claim 14, wherein the data includes high-priority data related to administrations of medication and low-priority data related to status of the container.

17. The container of claim 16, wherein the response is representative of a request to transmit high-priority data, if any, generated since a most recent synchronization with the electronic device.

18. The container of claim 14, further comprising:
   a cap that is designed to enclose the cavity when secured to the structural body.

19. The container of claim 18, wherein the memory, the communication circuitry, and the processor are included in the cap.

\* \* \* \* \*